(12) United States Patent
Radcliffe et al.

(10) Patent No.: US 12,178,719 B2
(45) Date of Patent: Dec. 31, 2024

(54) APPARATUS FOR ALIGNING AN ACETABULAR CUP

(71) Applicant: DEPUY IRELAND UNLIMITED COMPANY, County Cork (IE)

(72) Inventors: Sarah Radcliffe, Sheffield (GB); Stephanie Prince, Wakefield (GB); Duncan Young, Melbourn (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 434 days.

(21) Appl. No.: 17/456,269

(22) Filed: Nov. 23, 2021

(65) Prior Publication Data

US 2022/0079775 A1 Mar. 17, 2022

Related U.S. Application Data

(62) Division of application No. 15/781,543, filed as application No. PCT/EP2016/079884 on Dec. 6, 2016, now Pat. No. 11,207,195.

(30) Foreign Application Priority Data

Dec. 7, 2015 (GB) ...................... 1521501

(51) Int. Cl.
*A61F 2/46* (2006.01)
*A61B 17/56* (2006.01)
(Continued)

(52) U.S. Cl.
CPC ............ *A61F 2/4609* (2013.01); *A61B 17/56* (2013.01); *A61B 17/58* (2013.01); *A61F 2/34* (2013.01);
(Continued)

(58) Field of Classification Search
CPC ........ A61F 2/4609; B43L 13/08; G01B 3/563
See application file for complete search history.

(56) References Cited

U.S. PATENT DOCUMENTS 2,426,991 A * 9/1947 Emrich ................... B43L 13/08
33/434
4,057,902 A * 11/1977 Matsui ................... G01B 3/563
33/1 N
(Continued)

FOREIGN PATENT DOCUMENTS

EP 2294980 A1 3/2011
FR 2781362 A1 1/2000
(Continued)

*Primary Examiner* — Zade Coley
(74) *Attorney, Agent, or Firm* — Barnes & Thornburg LLP

(57) ABSTRACT

An apparatus and method for aligning an acetabular cup. The apparatus may include an acetabular cup and/or a protractor and/or a depth gauge tool and may be provided in the form of a surgical kit. Components of the apparatus may allow an angle of rotation of an acetabular cup about an axis of the cup relative to an anatomical feature of a patient to be determined when the acetabular cup implant is placed in the acetabulum of the patient. Components of the apparatus may allow an amount of overhang between a rim of an acetabular cup and an edge of the acetabulum to be determined. The acetabular cup may be an acetabular trial cup or and acetabular cup implant. Embodiments of the invention may allow both the angle of rotation about the cup axis and the amount of overhang between the rim and the acetabulum edge to be determined.

6 Claims, 16 Drawing Sheets

(51) Int. Cl.
  *A61B 17/58* (2006.01)
  *A61F 2/34* (2006.01)
  *A61F 2/42* (2006.01)
  *A61F 2/30* (2006.01)

(52) U.S. Cl.
  CPC ............... *A61F 2/42* (2013.01); *A61F 2/46* (2013.01); *A61F 2/468* (2013.01); *A61F 2002/30617* (2013.01); *A61F 2002/4668* (2013.01)

(56) References Cited

U.S. PATENT DOCUMENTS

| | | | | |
|---|---|---|---|---|
| 4,170,065 | A | * | 10/1979 | Hiscott ............... G01C 21/20 33/482 |
| 4,625,409 | A | * | 12/1986 | Arakawa ............ G06F 3/04845 33/471 |
| 4,795,469 | A | | 1/1989 | Oh |
| 5,408,753 | A | * | 4/1995 | Hong ................... B43L 13/08 33/430 |
| 5,507,824 | A | | 4/1996 | Lennox |
| 6,568,098 | B1 | * | 5/2003 | Beckhart ............... H01L 21/68 33/645 |
| 7,210,237 | B1 | * | 5/2007 | Shih .................... B43L 13/002 33/534 |
| 8,585,769 | B2 | | 11/2013 | Vankoski |
| 8,764,845 | B2 | | 7/2014 | Brooks |
| 8,894,717 | B2 | | 11/2014 | Birkbeck et al. |
| 8,979,939 | B2 | | 3/2015 | Birkbeck et al. |
| 9,474,614 | B2 | | 10/2016 | Kelley |
| 2005/0060040 | A1 | | 3/2005 | Auxepaules |
| 2005/0228395 | A1 | | 10/2005 | Auxepaules |
| 2006/0002810 | A1 | | 1/2006 | Grohowski |
| 2006/0015186 | A1 | | 1/2006 | Isaac |
| 2007/0113415 | A1 | * | 5/2007 | Shih .................... G01B 3/563 33/471 |
| 2007/0162146 | A1 | | 7/2007 | Balay |
| 2007/0219562 | A1 | | 9/2007 | Slone |
| 2009/0234459 | A1 | | 9/2009 | Sporring |
| 2010/0191339 | A1 | | 7/2010 | Brooks |
| 2010/0262144 | A1 | | 10/2010 | Kelman |
| 2011/0093087 | A1 | | 4/2011 | Mcmahon |
| 2012/0185059 | A1 | * | 7/2012 | Vankoski ............ A61F 2/4684 623/22.24 |
| 2014/0249535 | A1 | * | 9/2014 | McCarthy ........... A61F 2/4684 606/91 |
| 2015/0045905 | A1 | | 2/2015 | Kelley |
| 2015/0289992 | A1 | * | 10/2015 | Anglin ................ A61F 2/4657 606/91 |
| 2015/0313724 | A1 | | 11/2015 | Jackson, III |

FOREIGN PATENT DOCUMENTS

| | | |
|---|---|---|
| WO | WO 2003037192 A1 | 5/2003 |
| WO | WO 2010099247 A2 | 9/2010 |
| WO | WO 2010122281 A1 | 10/2010 |
| WO | WO 2012154407 A2 | 11/2012 |
| WO | WO 2014063226 A1 | 5/2014 |
| WO | WO 2014153530 A1 | 9/2014 |
| WO | WO 2015/100461 A1 | 7/2015 |

* cited by examiner

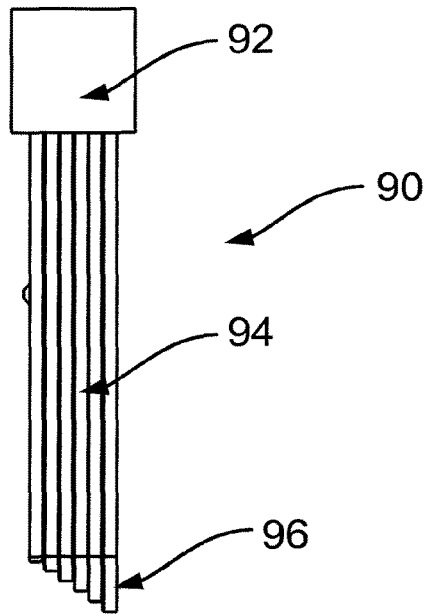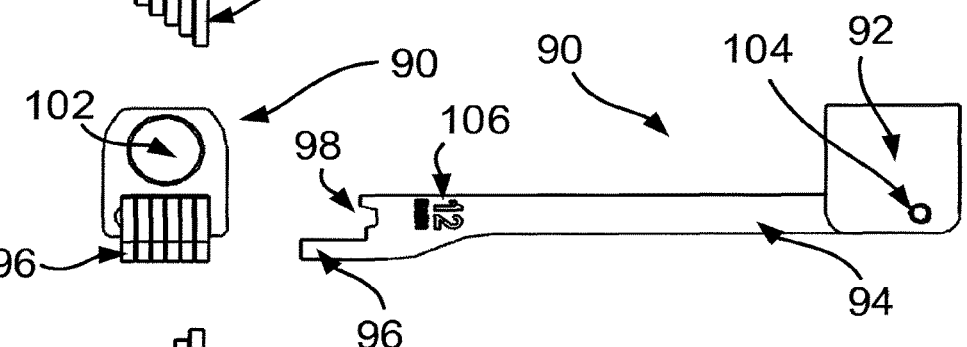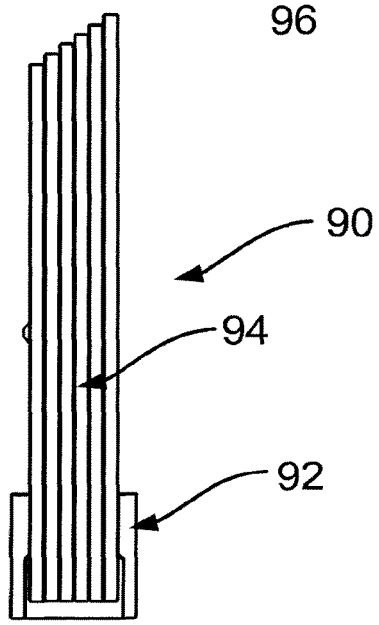

APPARATUS FOR ALIGNING AN ACETABULAR CUP

CROSS REFERENCE TO RELATED PCT APPLICATION

This application is a divisional to U.S. patent application Ser. No. 15/781,543, filed Jun. 5, 2018, which is a National Stage 35 U.S.C. 371 of International Patent Application PCT/EP2016/079884 filed Dec. 6, 2016, which claims priority to United Kingdom Application No. GB1521501.5, filed Dec. 7, 2015, now abandoned, all of which are incorporated by reference in their entireties.

FIELD OF THE INVENTION

This invention relates to an apparatus and method for aligning an acetabular cup. In particular, this invention relates to an acetabular cup, a protractor, a depth gauge tool, a surgical kit and a corresponding method.

BACKGROUND OF THE INVENTION

Hip replacement is a surgical procedure in which the hip joint is replaced by a prosthetic implant. Total replacement of the hip joint involves installing an acetabular cup implant in the acetabulum of a patient and installing a prosthetic in the femur of the patient. A ball of the prosthetic is received in the acetabular cup implant.

Successful hip replacement surgery requires correct alignment of the acetabular cup implant. Misalignment of the acetabular cup implant may result is restricted movement of the prosthetic and/or accelerated wear and tear of the bearing surfaces of the acetabular cup implant and the ball of the prosthetic.

Hip replacement surgery usually involves the use of an acetabular trial cup. The acetabular trial cup is used to prepare the acetabulum for receiving the acetabular cup implant. The trial cup may be used by a surgeon to evaluate the cavity that has been prepared in the bone. The fit of the trial cup may mimic the fit of the acetabular cup implant, so that the surgeon can check tightness (press-fit) and depth. The trial cup may also be used to judge whether the acetabular cup implant will allow for free and correct movement of the prosthetic when the ball of the prosthetic is received in the acetabular cup implant. After the surgeon is satisfied that the acetabular trial cup is correctly positioned and aligned, the trial cup may be removed from the acetabulum and replaced with the acetabular cup implant itself When the acetabular cup implant is placed in the acetabulum, its position and alignment may not match that of the acetabular trial cup. Oftentimes surgeons may simply judge the position and orientation of the acetabular cup implant to match the approximate position and orientation of the acetabular trial cup as they remember it. However, it is known to provide features such as horizon markings on the acetabular trial cup and/or the acetabular cup implant to aid the surgeon in matching the alignment of the acetabular cup implant with that of acetabular trial cup.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided an acetabular cup comprising:
a substantially hemispherical shell having a rim, wherein a cup axis of the acetabular cup passes through a pole of the substantially hemispherical shell and is substantially perpendicular to a plane containing the rim; and
a plurality of markings located around the rim for determining an angle of rotation of the acetabular cup about the cup axis relative to at least one anatomical feature of a patient when the acetabular cup is placed in an acetabulum of the patient.

The provision of markings located around the rim of the acetabular cup may conveniently allow a surgeon to determine an angle of rotation of the acetabular cup about the cup axis relative to at least one anatomical feature of a patient. The markings may, for example, allow a surgeon to determine the orientation of an acetabular trial cup during surgery. The orientation of the trial cup may be recorded and subsequently used to orientate an acetabular cup implant.

Where the cup is an acetabular cup implant, the markings may allow the surgeon to orientate the implant correctly, according to the desired orientation previously determined as part of a pre-operative plan and/or using a trial cup that may also include such markings as noted above.

The plurality of markings located around the rim may include a first marking for determining an angle of rotation of the acetabular cup relative to a first anatomical feature of the patient and a plurality of further markings for determining an angle of rotation of the acetabular cup relative to a further anatomical feature of the patient. In this way, the first marking may be aligned with a larger or more prominent anatomical feature (e.g. the anterior superior iliac spine (ASIS)), while the further markings may be used to align with smaller, more local anatomical feature such as an osteophyte at an edge of the acetabulum.

The first marking may be a notch in the rim of the substantially hemispherical shell. The further markings may include a plurality of tick marks positioned around at least a part of the rim. The tick marks may be equally spaced (e.g. in increments of 1, 2, 5 or 10 degrees), so as to provide regular indications of angle around the rim.

The plurality of markings located around the rim may be provided in at least two separate groups. The groups may be positioned so that they allow convenient alignment with certain anatomical features.

At least some of the markings located around the rim for determining an angle of rotation of the acetabular cup may be provided on the rim of the acetabular cup. In some examples, the markings may be provided on an outer surface of the substantially hemispherical shell (e.g. along with the horizon markings described below). These approaches may be combined, whereby markings may be provided both on the rim and on the outer surface of the substantially hemispherical shell.

A plurality of horizon markings may be located around an outer surface of the substantially hemispherical shell for determining an amount of overhang between the rim of the acetabular cup and an edge of the acetabulum of the patient. Combined use of the markings for determining an angle of rotation of the acetabular cup about the cup axis relative to at least one anatomical feature of the patient and the horizon markings may allow the precise orientation of the acetabular cup to be determined.

Further horizon markings may be provided on the outer surface of the substantially hemispherical shell. The horizon markings may be located around a first side of the shell for determining an amount of overhang of a superior-posterior portion of the acetabular cup and the further horizon markings may be located around an opposite side of the substantially hemispherical shell for determining an amount of overhang of an anterior portion of the acetabular cup.

The horizon markings may each include a plurality of steps. Each step may extend a predetermined distance from the rim of the cup towards the pole of the substantially hemispherical shell. A location of an edge of each step distal the rim may be indicative of an amount of overhang between the rim of the acetabular cup and the edge of the acetabulum.

In some embodiments, the stepped horizon markings may be spaced around the rim of the acetabular cup. The plurality of markings located around the rim for determining an angle of rotation of the acetabular cup about the cup axis relative to at least one anatomical feature of a patient may comprise the stepped horizon markings. In this way, the stepped horizon markings may be used to determine both the amount of overhang and the angle of rotation of the acetabular cup about the cup axis relative to the at least one anatomical feature.

An acetabular cup (e.g. acetabular trial cup or acetabular cup implant) of the kind described herein may be manufactured by metal injection molding (MIM).

The acetabular cup may be an acetabular trial cup. The features of the acetabular trial cup may allow the orientation of the acetabular trial cup to be accurately determined. This position (e.g. the angle determined using the markings around the rim and optionally also the amount of overhang as determined using the horizon markings) may be noted so that they may be reproduced when the acetabular trial cup is replaced with the acetabular cup implant.

The acetabular cup may be an acetabular cup implant. The features of the acetabular cup implant may allow the orientation of the acetabular trial cup to be accurately determined.

For instance, the angle determined using the markings around the rim and optionally also the amount of overhang as determined using the horizon markings may be adjusted to match those recorded previously in respect of a correctly aligned acetabular trial cup.

According to another aspect of the invention, there is provided a surgical kit comprising an acetabular trial cup and an acetabular cup implant of the kind described above.

Alternative approaches to determining an angle of rotation of the acetabular cup about the cup axis relative to at least one anatomical feature of a patient are envisaged.

According to a further aspect of the invention, there is provided a protractor for use with an acetabular cup, wherein the protractor comprises:
  a body portion having an upper surface and a lower surface, wherein the lower surface is configured to engage with a rim of the acetabular cup such that a centre of the body portion is aligned with a cup axis of the acetabular cup; and
  a plurality of markings located around a periphery of the body portion on the upper surface, for determining an angle of rotation of the acetabular cup about the cup axis relative to at least one anatomical feature of a patient when the acetabular cup is placed in an acetabulum of the patient and the body portion is positioned over said rim.

The markings on the protractor may conveniently allow a surgeon to determine an angle of rotation of the acetabular cup about the cup axis relative to at least one anatomical feature of a patient.

The protractor may be used with an acetabular trial cup and/or with an acetabular cup implant. When used with an acetabular trial cup, the protractor may allow a surgeon to determine the orientation of the acetabular trial cup during surgery. The orientation of the trial cup may be recorded and subsequently used to orientate an acetabular cup implant.

When used with an acetabular cup implant, the protractor may allow the surgeon to orientate the implant correctly, according to a desired orientation previously determined as part of a pre-operative plan and/or using a trial cup.

The protractor may include at least one member extending beneath the body portion to hang over the rim of the acetabular cup for determining an amount of overhang between the rim of the acetabular cup and an edge of the acetabulum of the patient. Combined use of the markings for determining an angle of rotation of the acetabular cup about the cup axis relative to at least one anatomical feature of the patient and the at least one member extending beneath the body portion may allow the precise orientation of the acetabular cup to be determined.

A plurality of engagement portions may be located on the lower surface of the body portion for engaging with corresponding engagement portions of the acetabular cup to prevent rotation of the protractor relative to the acetabular cup about the cup axis. This may prevent movement of the protractor relative to the acetabular cup, which could otherwise lead to incorrect determinations of the orientation of the acetabular cup.

The markings may comprise a plurality of tick marks located around a periphery of the body portion on the upper surface. The tick marks may be substantially equally spaced (e.g. in increments of 1, 2, 5 or 10 degrees), so as to provide regular indications of angle.

The markings located around a periphery of the body portion on the upper surface may be provided in at least two separate groups. The groups may be positioned so that they allow convenient alignment with certain anatomical features.

According to another aspect of the invention, there is provided a surgical kit comprising an acetabular cup and a protractor of the kind described above.

The acetabular cup of the surgical kit may be an acetabular trial cup or an acetabular cup implant. In some examples, the kit may include both an acetabular trial cup and an acetabular cup implant. The protractor may, for instance, initially be used to determine the orientation of the acetabular trial cup and then transferred to the acetabular cup implant to match the orientation of the acetabular cup implant with that determined for the acetabular trial cup.

In some examples, a surgical kit of the kind described herein may further include a rim calliper for determining an amount of overhang between a rim of the acetabular cup and an edge of the acetabulum of the patient. In such examples, the protractor described above need not necessarily include the at least one member extending beneath the body portion, since the rim calliper may be used instead. Similarly, the acetabular cup(s) of such a surgical kit need not necessarily include horizon markings.

Alternative approaches for determining the correct amount of overhang between the rim of an acetabular cup implant and the edge of the acetabulum are envisaged.

According to a further aspect of the invention, there is provided a depth gauge tool for use with an acetabular cup implant, the depth gauge tool comprising:
  a base including an aperture for receiving an impactor for pushing the acetabular cup implant into an acetabulum of a patient;

a plurality of elongate arms pivotably attached to the base, wherein an end of each elongate arm distal the base includes:
an abutment surface for abutting a rim of the acetabular cup implant; and
a finger configured to extend over the rim of the acetabular cup implant to abut an edge of the acetabulum of the patient for determining an amount of overhang between the rim of the acetabular cup implant and the edge of the acetabulum,
wherein the finger of each elongate arm of the depth gauge tool has a different length.

The surgeon may select one of the plurality of elongate arms to use based on the correct amount of overhang previously determined as part of a pre-operative plan and/or using an acetabular trial cup.

According to another aspect of the invention, there is provided a surgical kit comprising at least one acetabular cup implant and a depth gauge tool of the kind described above.

It is envisaged that the angle of rotation of the acetabular cup implant may be determined using markings around the rim of the acetabular cup implant of the kind described above or alternatively using a protractor of the kind described above.

The kit may further include an acetabular trial cup and a rim calliper for determining an amount of overhang between a rim of the acetabular trial cup and an edge of the acetabulum of the patient. Alternatively, the acetabular trial cup may be an acetabular trial cup of the kind described above, including markings around the rim thereof and possibly as horizon markings.

According to a further aspect of the invention, there is provided a method of determining the alignment of an acetabular cup, wherein the acetabular cup comprises a substantially hemispherical shell having a rim, wherein a cup axis of the acetabular cup passes through a pole of the substantially hemispherical shell and is substantially perpendicular to a plane containing the rim, the method comprising:
placing the acetabular cup in an acetabulum of the patient; and
using a plurality of markings located around the rim of the acetabular cup to determine an angle of rotation of the acetabular cup about the cup axis relative to at least one anatomical feature of the patient.

The acetabular cup may for instance be an acetabular trial cup or an acetabular cup implant.

The markings located around the rim of the acetabular cup may conveniently allow a surgeon to determine an angle of rotation of the acetabular cup about the cup axis relative to at least one anatomical feature of a patient. The markings may, for example, allow a surgeon to determine the orientation of an acetabular trial cup during surgery. The orientation of the trial cup may be recorded and subsequently used to orientate an acetabular cup implant.

Where the cup is an acetabular cup implant, the markings may allow the surgeon to orientate the implant correctly, according to the desired orientation previously determined as part of a pre-operative plan and/or using a trial cup that may also include such markings as noted above.

Determining the alignment of the acetabular cup further may comprise using a plurality of horizon markings located around an outer surface of the substantially hemispherical shell to determine an amount of overhang between the rim of the acetabular cup and an edge of the acetabulum of the patient. As mentioned above, this combined approach may allow the orientation of the acetabular cup to be determined precisely.

The method may further include using the plurality of markings located around the rim of the acetabular cup to determine a position at which to measure the amount of overhang between the rim of the acetabular cup and the edge of the acetabulum of the patient using the horizon markings. This may allow errors, associated with the fact that the amount of overhang may vary with angle around the rim of the acetabular cup, to be avoided.

According to another aspect of the invention, there is provided a method of determining the alignment of an acetabular cup, the method comprising:
placing the acetabular cup in an acetabulum of the patient;
providing a protractor comprising a body portion having an upper surface and a lower surface;
engaging the lower surface of the body portion with a rim of the acetabular cup so that a centre of the body portion is aligned with a cup axis of the acetabular cup; and
using a plurality of markings located around a periphery of the body portion on the upper surface to determine an angle of rotation of the acetabular cup about the cup axis relative to at least one anatomical feature of the patient.

The markings on the protractor may thus conveniently allow a surgeon to determine an angle of rotation of the acetabular cup about the cup axis relative to at least one anatomical feature of a patient.

The protractor may be used with an acetabular trial cup and/or with an acetabular cup implant. When used with an acetabular trial cup, the method may allow a surgeon to determine the orientation of the acetabular trial cup during surgery. The method may include recording the orientation of the trial cup and subsequently using the recorded orientation to orientate an acetabular cup implant.

When used with an acetabular cup implant, the method may allow the surgeon to orientate the implant correctly, according to a desired orientation previously determined as part of a pre-operative plan and/or using a trial cup.

The acetabular cup may for instance be an acetabular trial cup or an acetabular cup implant.

The method may further include using at least one member extending beneath the body portion and overhanging the rim of the acetabular cup to determine an amount of overhang between the rim of the acetabular cup and an edge of the acetabulum of the patient. Again, as mentioned above, this combined approach may allow the orientation of the acetabular cup to be determined precisely.

According to a further aspect of the invention, there is provided a method of determining the alignment of an acetabular cup implant, the method comprising:
placing the acetabular cup implant in an acetabulum of the patient;
providing a depth gauge tool comprising a base including an aperture and a plurality of elongate arms pivotably attached to the base, wherein an end of each elongate arm distal the base includes:
an abutment surface for abutting a rim of the acetabular cup implant; and
a finger configured to extend over the rim of the acetabular cup implant to abut an edge of the acetabulum of the patient, wherein the finger of each elongate arm of the depth gauge tool has a different length;

providing an impactor for pushing the acetabular cup implant into the acetabulum; inserting the impactor through the aperture of the base;

placing a distal end of the impactor against a pole of the acetabular cup implant;

selecting one of the elongate arms according to a required depth;

abutting the abutment surface of the selected elongate arm against the rim of the acetabular cup implant; and abutting an end of the finger of the elongate arm against an edge of the acetabulum of the patient.

The surgeon may select one of the plurality of elongate arms to use based on the correct amount of overhang previously determined as part of a pre-operative plan and/or using an acetabular trial cup.

BRIEF DESCRIPTION OF THE DRAWINGS

Embodiments of the present invention will be described hereinafter, by way of example only, with reference to the accompanying drawings in which like reference signs relate to like elements and in which:

FIGS. 10A-10F show an example of a rim gauge in accordance with an embodiment of the invention;

DETAILED DESCRIPTION

Embodiments of the present invention are described in the following with reference to the accompanying drawings.

Embodiments of this invention can allow the rotational alignment of an acetabular cup, such as an acetabular cup implant or an acetabular trial cup, about a cup axis of the cup to be determined. Embodiments of this invention can also allow the orientation of an acetabular cup relative to the inclination and/or anteversion axes to be determined. The orientation of the acetabular cup relative to the inclination and anteversion axes may be determined by measuring an amount of overhang between the rim of an acetabular cup and an edge of the acetabulum of a patient in one or more locations around the rim. The location(s) around the rim at which the measurement(s) are made for determining the amount of overhang can also be determined.

In certain embodiments, the approaches as noted above can be combined to allow accurate determination of the orientation of the acetabular cup in terms of its angle of rotation within the acetabulum (about the cup axis) and its orientation relative to the inclination and anteversion axes. In some examples, the features described herein for determining the orientation of the acetabular cup may be used initially to record the desired orientation of an acetabular trial cup. The recorded orientation may then be used correctly to orient an acetabular cup implant.

Figure 1:
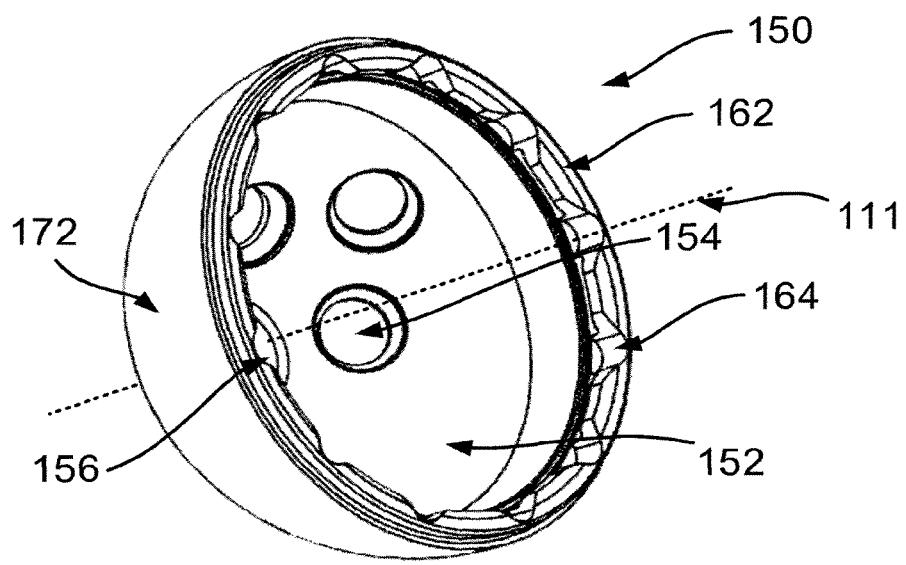
FIG. 1 shows an example of an acetabular cup.

FIG. 1 shows an example of an acetabular cup implant 150. The acetabular cup implant 150 is configured to be received within the acetabulum of a patient. The implant 150 includes a substantially hemispherical shell having an inner surface 152 and an outer surface 172. The implant 150 also includes a rim 162. The rim 162 is substantially circular.

The implant 150 further includes a number of openings 154 provided in the substantially hemispherical shell for facilitating attachment of the implant 150 to the acetabulum using screws or other fixings that pass through the openings 154 into the pelvis.

An opening 156 is located at a pole of the substantially hemispherical shell for receiving a tool such as in impactor for allowing a surgeon to insert the implant 50 into the acetabulum (either by manually pushing down on the tool and/or by striking the tool at a proximal end thereof).

The acetabular cup implant 150 has a cup axis 111 that passes through a pole of the substantially hemispherical shell. The cup axis 111 is substantially perpendicular to the plane containing the rim 162.

The implant 150 may further include a plurality of engagement portions 164. These engagement portions 164 may, as described below, be configured to engage with corresponding engagement portions on a protractor to avoid movement of the protractor relative to the hemispherical shell (which may otherwise lead to an incorrect determination of the angle of rotation of the implant 150 within the acetabulum).

Figure 2A:
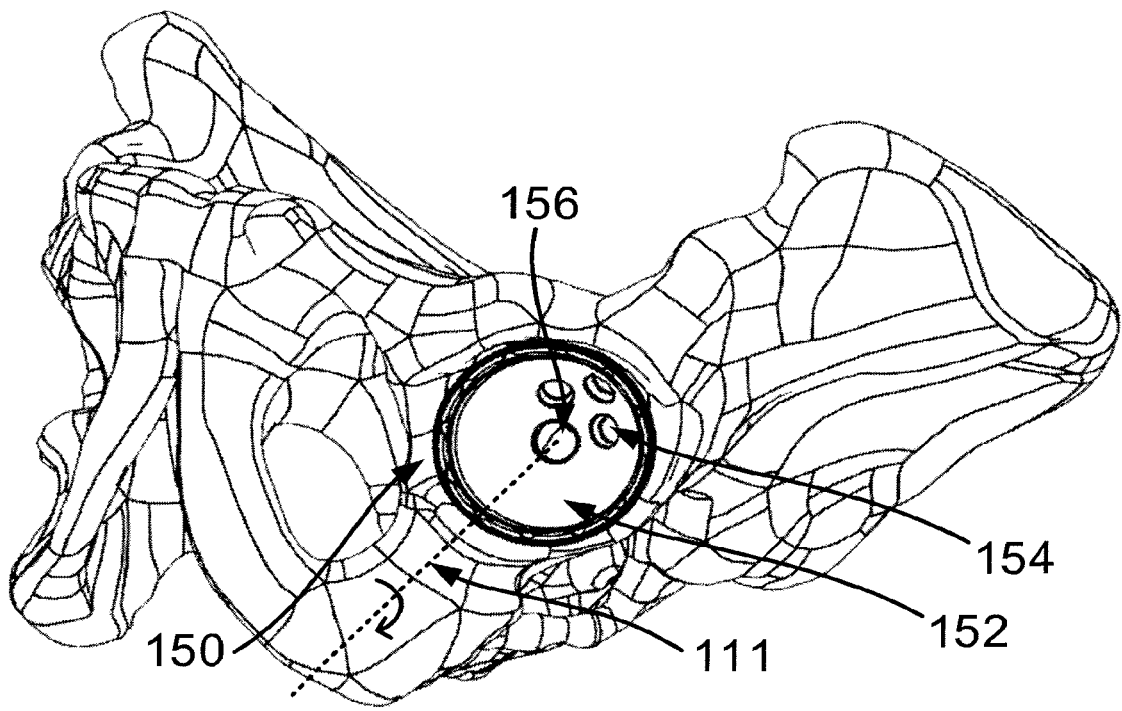
FIGS. 2A and 2B show a pelvis having the acetabular cup of FIG. 1 located in an acetabulum thereof.
Figure 2B:
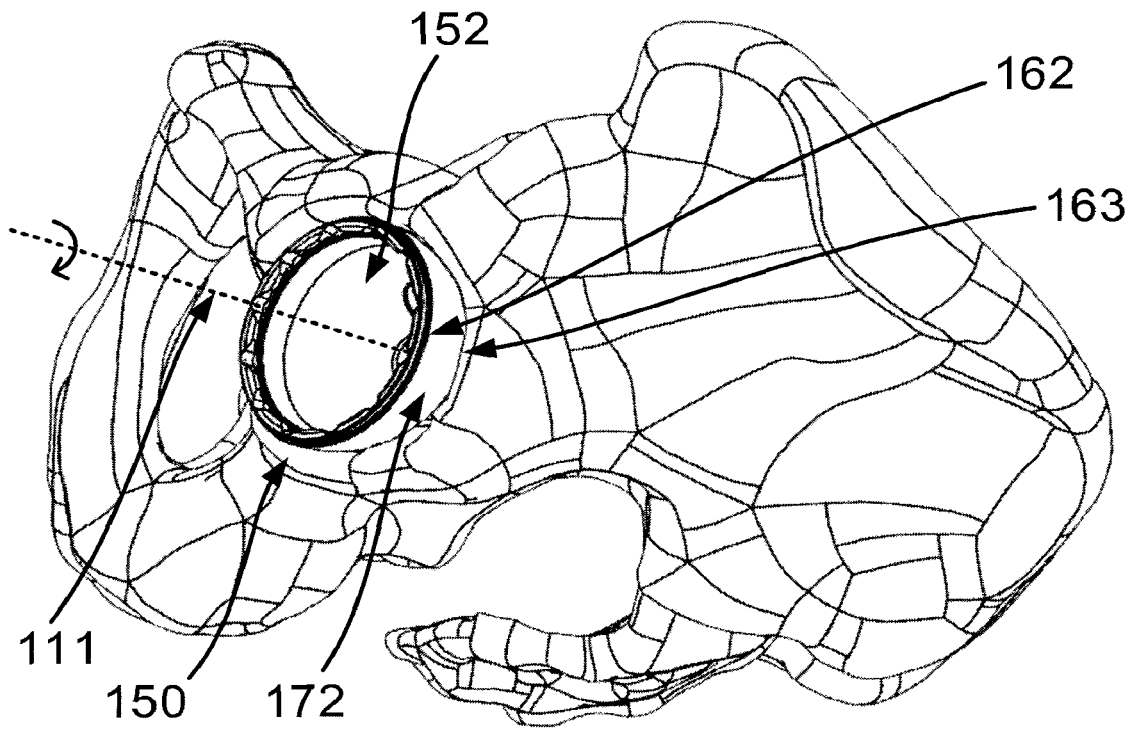

FIGS. 2A and 2B each show the pelvis of a patient with an acetabular cup implant 150 of the kind shown in FIG. 1 in an acetabulum 200 thereof. From FIGS. 2A and 2B it can be seen that the rotation of the implant 150 about its cup axis 111 may, for example, influence the positions of the openings 154. The correct angle of rotation of the implant 150 may have been determined during pre-operative planning and/or earlier in the surgical procedure using an acetabular trial cup as will be described below. Therefore, for correct orientation of the implant 150 within the acetabulum, it may be desirable to allow the angle of rotation of the implant 150 about the cup axis 111 to be determined relative to one or more anatomical features of the patient. The anatomical features may thus be used as a reference point for determining the angle of rotation of the implant 150 about the cup axis 111. These anatomical features may, for instance, include features of the pelvis such as the anterior superior iliac spine (ASIS), or osteophytes located at the edge acetabulum.

From FIG. 2B, it is also clear that at certain positions around the rim 162 of the implant 150 there is an amount of overhang between the rim 162 of the implant 150 and an edge 163 of the acetabulum. This amount of overhang can be used to determine an orientation of the implant 150 relative to the anteversion and/or inclination axes. Again, the correct orientation of the implant 150 relative to the anteversion and/or inclination axes may have been determined during pre-operative planning and/or using a trial cup.

As will be described in more detail below, embodiments of this invention can allow both the angle of rotation of the implant 150 about the cup axis 111 and the orientation of the implant 150 relative to the inclination and anteversion axes to be determined.

Figure 3A:
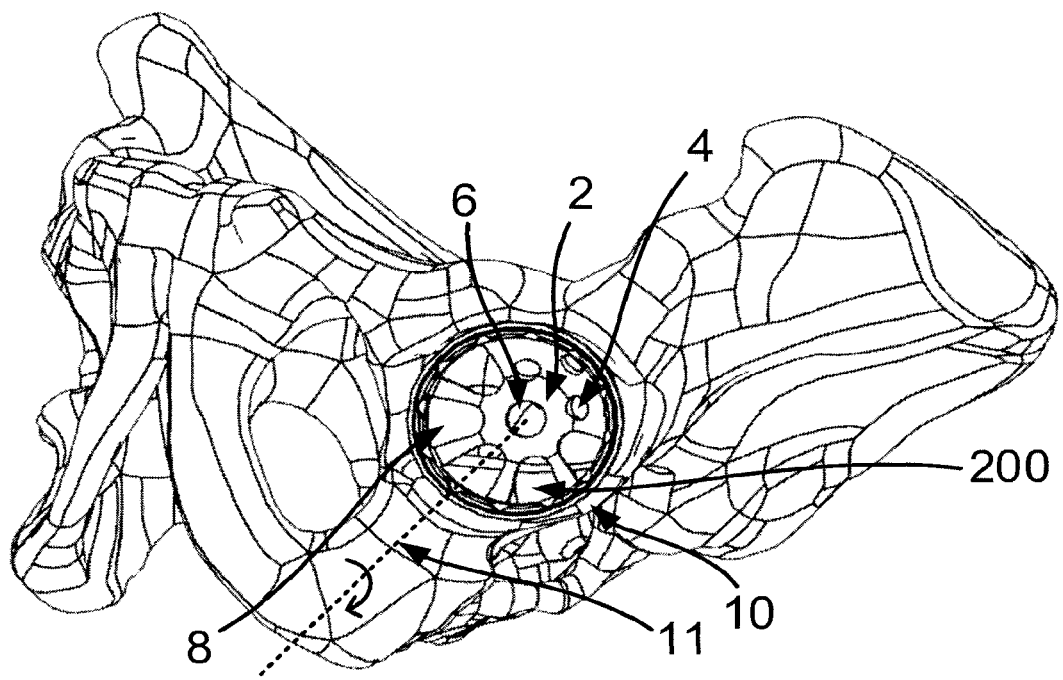
FIGS. 3A and 3B show a pelvis having the trial cup located in an acetabulum thereof.
Figure 3B:
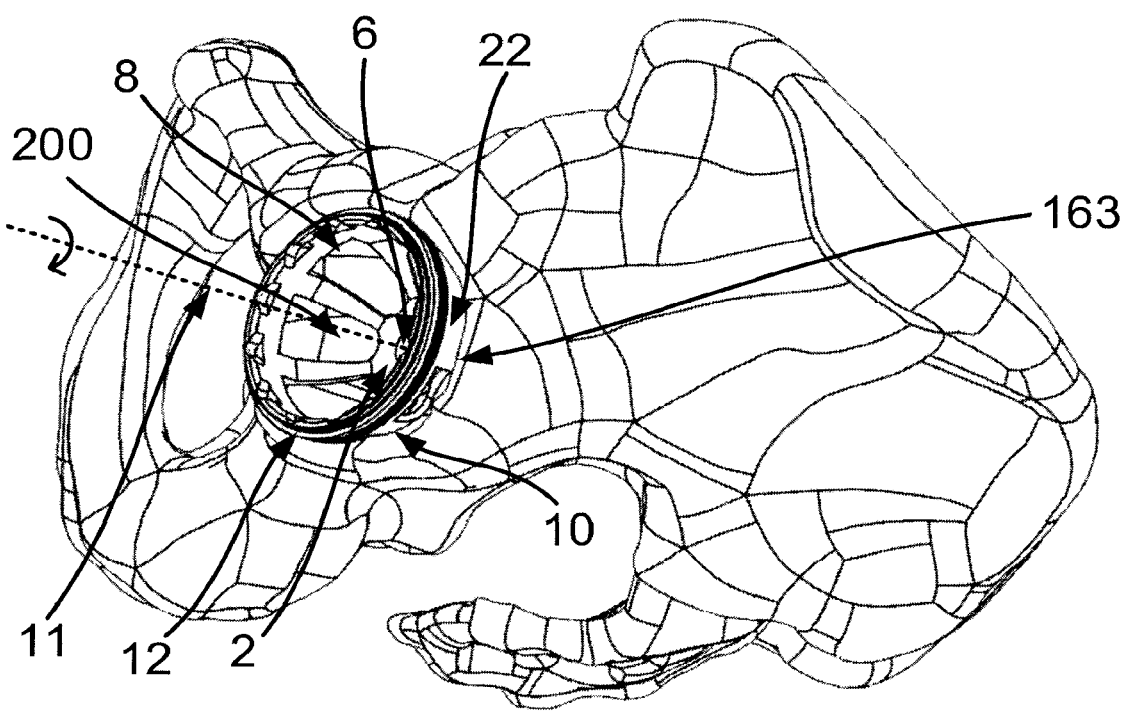

FIG. 3A and FIG. 3B shows the pelvis of a patient with an acetabular trial cup 10 in an acetabulum 200 thereof. The trial cup 10 has a number of features in common with the implant 150 described above. Thus, the trial cup includes a substantially hemispherical shell having an inner surface 2 and a rim 12. The trial cup 10 has a cup axis 11 that passes through a pole of the substantially hemispherical shell and that is substantially perpendicular to a plane containing the rim 12. The trial cup 10 may also include openings 4, 6, which are similar to the openings 154, 156 described above in relation to FIG. 1.

The trial cup 10 may further include a number of openings 8 in the substantially hemispherical shell to allow inspection of the underlying acetabulum 200 when the trial cup 10 is in place. As has been mentioned above, features of this invention may allow the orientation of an acetabular cup such as an acetabular cup implant or an acetabular trial cup to be determined. As will be described in more detail below, it is envisaged that an acetabular trial cup 10 of the kind shown in FIGS. 3A and 3B may be used to determine the correct orientation for an acetabular cup implant 150 of the kind shown in FIG. 1. The features of this invention described herein below may allow, for example, the angle of rotation of the trial cup 10 around the cup axis 11 and/or the amount of overhang between the rim 12 and an edge 163 of the acetabulum 200 to be determined. These measurements, determined using the trial cup 10, may then be used correctly to orientate an acetabular cup implant 150 of the kind shown in FIG. 1 in the acetabulum 200.

Figure 4:
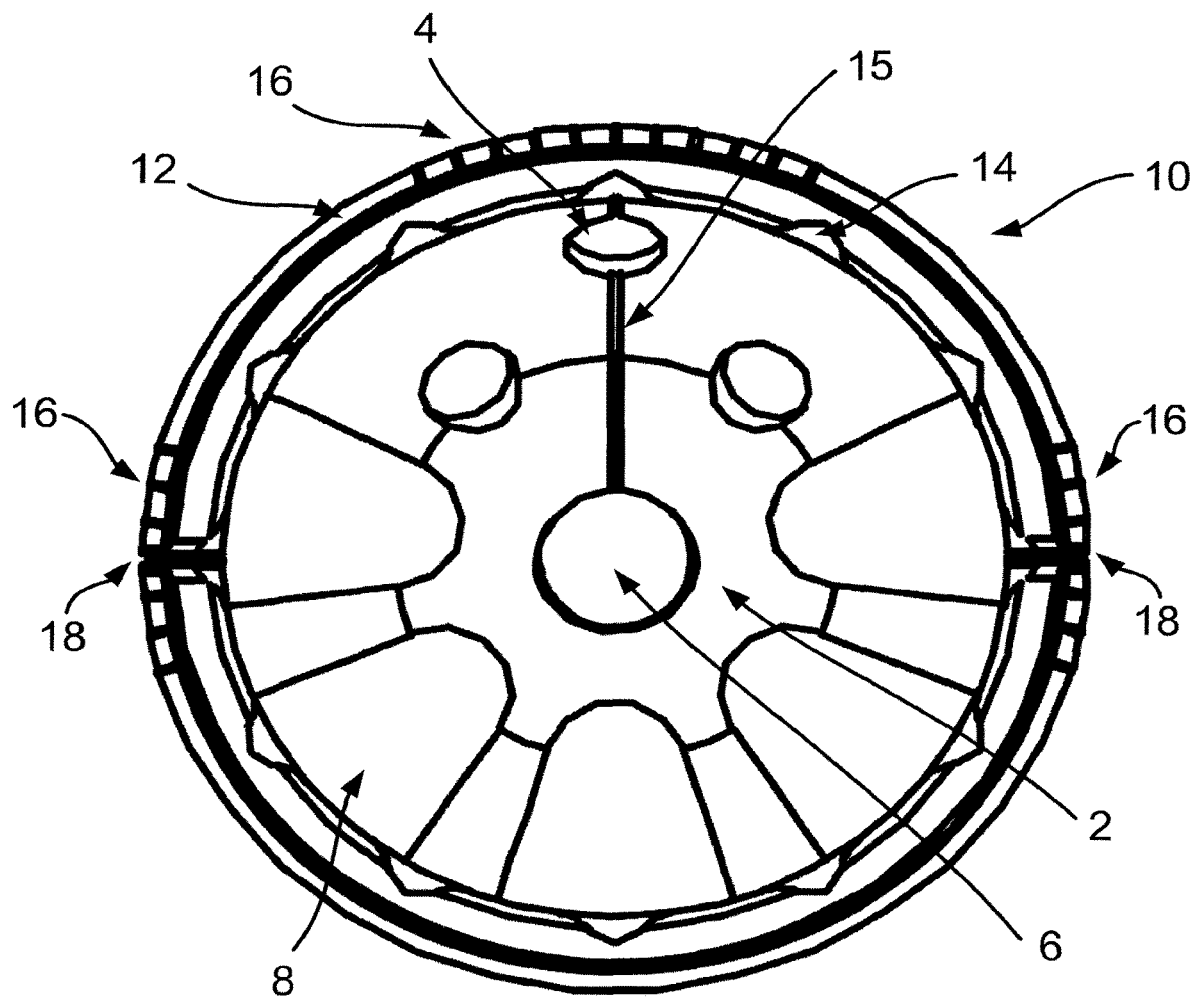
FIGS. 4-6 show an example of a trial cup in accordance with an embodiment of the invention.
Figure 5:
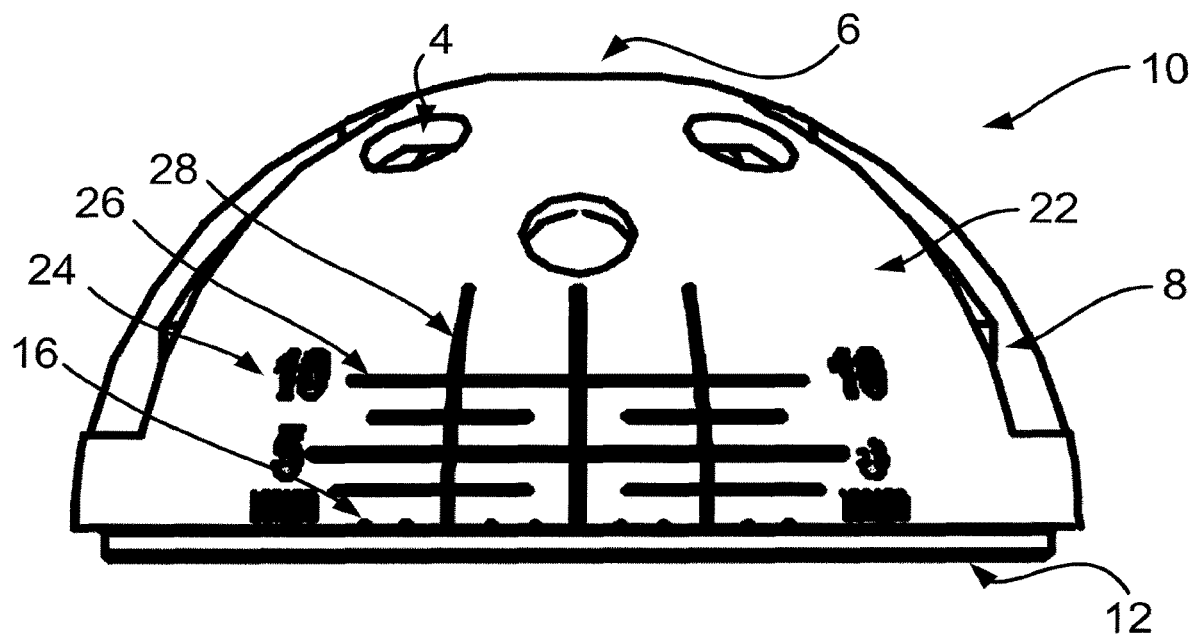
Figure 6:
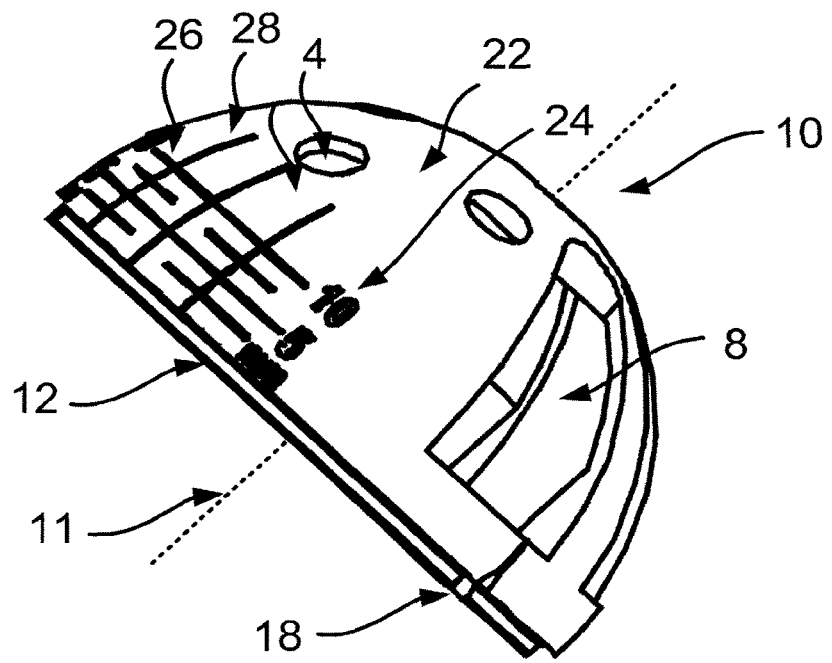

FIGS. 4-6 shown an example of an acetabular cup according to an embodiment of this invention. In the present example, the acetabular cup is an acetabular trial cup 10. However, it is envisaged that features of the trial cup 10 described here may also be incorporated into an acetabular cup implant of the kind described above in relation to FIG. 1.

The acetabular trial cup 10 has a substantially hemispherical shell that has an inner surface 2 and an outer surface 22. As described above in relation to the implant 150 in FIGS. 1 and 2 and the trial cup 10 in FIG. 3, the acetabular trial cup 10 of the present embodiment may include a number of openings 4. These openings 4 may match the positions of corresponding openings in an acetabular cup implant of the kind shown in FIG. 1, to aid the trialling process. Similarly, the trial cup 10 may include an opening 6 similar to the opening 156 described above in relation to the implant 150 in FIGS. 1 and 2 and the opening 6 described above in relation to the trial cup 10 in FIG. 3. The trial cup 10 may further include a number of openings 8 positioned around the substantially hemispherical shell. Again as described above in relation to the trial cup 10 in FIG. 3, these opening 8 may allow for greater visibility of the underlying acetabulum while the trial cup 10 is being used.

The trial cup 10 has a rim 12. A number of engagement portions 14 may be positioned around the rim 12. These engagement portions 14 may allow for engagement of the rim 12 of the trial cup 10 with corresponding engagement portions of, for example, a protractor of the kind described below in relation to FIGS. 7 and 8.

The acetabular trial cup 10 has a cup axis 11. The cup axis is shown schematically by the dotted line labelled 11 in FIG. 6. As can be seen in FIG. 6, the cup axis 11 passes through the pole of the substantially hemispherical shell of the trial cup 10 and is substantially perpendicular to a plane containing the rim 12.

The trial cup 10 of the present embodiment includes a plurality of markings 16, 18, which are located around the rim 12 for determining an angle of rotation of the acetabular trial cup 10 about the cup axis 11, relative to at least one anatomical feature of a patient when the acetabular trial cup 10 is placed in an acetabulum of the patient. Although the markings 16, 18 are described here in the context of an acetabular trial cup, it is envisaged that markings 16, 18 of this kind may be provided on an acetabular cup implant (for instance of the kind described above in relation to FIG. 1), to allow the angle of rotation of the cup implant about its cup axis to be determined.

During surgery, the markings 16, 18 may be used to determine the angle of rotation of the trial cup 10 about the cup axis 11, relative to one or more anatomical features of the patient. For instance, once the trial cup 10 has been correctly positioned within the acetabulum, the position of one or more anatomical features of the patient (e.g. the ASIS and/or one or more osteophytes) relative to one or more of the markings 16, 18 may be noted. Although not shown in the present embodiment, it is envisaged that the markings 16, 18 may be provided with numerical indications of angle, to allow convenient reading off of the angular positions of the one or more anatomical features.

The markings 16, 18 may include a first kind of marking 18 and a second kind of marking 16. The first markings 18 may be more prominent on the rim 12 than the second markings 16, which may be smaller. In one example, the markings 18 may take the form of a notch provided in the rim 12. The markings 16 may take the form of smaller notches or tick marks. The markings 16 may be, for instance, engraved or painted on the trial cup 10, or may be formed on the trial cup 10 using laser marking. The markings 18 may be used to denote prominent angles. For instance, the markings 18 may be provided at 90° intervals around the rim 12. The second markings 16 may be used to indicate smaller angular increments (e.g. 1°, 2° or 5° increments) than the markings 18. The First markings 18 and or the second markings 16 may be equally spaced.

The markings 16, 18 may in some examples be provided around the complete rim 12. However, it is envisaged that the markings 16, 18 may only occupy a part of the rim 12 as shown in FIG. 4. As also shown in FIG. 4, it is envisaged that the marking 16, 18 may be provided in one or more groups. These groups may located for convenient alignment with the anatomical features of the patient for determining the orientation of the trial cup relative to those features.

In the example shown in FIGS. 4-6, the markings 16, 18 are provided on the edge of the rim 12. However, it is envisaged that the markings 16, 18 may be provided anywhere around the rim 12 (for instance on the inner surface 2 or the outer surface 22 of the substantially hemispherical shell, adjacent the rim 12).

In this example, the trial cup 10 includes a primary clocking mark 15 (indicated in FIG. 4). This primary clocking mark 15 may be used to indicate the location of one of the openings 4 (e.g. a middle one of the openings 4, in the present example).

As explained previously, the openings 4 may be provided to facilitate attachment of an acetabular cup implant to the acetabulum using screws or other fixings that pass through the openings 4 into the pelvis—they may be provided also in a trial cup as shown in FIG. 4, for the surgeon to determine the correct locations of the openings 4 while noting the angle of rotation of the trial cup 10 about the cup axis 11 as described herein.

In the present example, primary clocking mark 15 extends from the pole of the substantially hemispherical shell of the trial cup 10 to the rim 12, and is aligned with a center of the middle opening 4. The primary clocking mark 15 may also be aligned with one of the markings 16, 18 provided around the rim 12, so that a surgeon may conveniently note the position of the middle opening 4 by viewing the markings 16, 18.

As can be seen in FIGS. 5 and 6, the acetabular trial cup 10 in this example also includes a plurality of horizon markings 26. The horizon markings 26 are located on the outer surface 22 of the substantially hemispherical shell of the trial cup 10. These horizon markings 26 may be used for determining an amount of overhang between the rim 12 of the trial cup 10 and an edge of the acetabulum of the patient when the trial cup 10 is received within the acetabulum of the patient.

Although the horizon markings 26 are described here in the context of an acetabular trial cup 10, it is envisaged that horizon markings of this kind may be provided on an acetabular cup implant (for instance of the kind described above in relation to FIG. 1), to allow an amount of overhang between the rim of the acetabular cup implant and an edge of the acetabulum of the patient to be determined when the acetabular cup implant is received within the acetabulum of the patient.

The horizon markings 26 can be provided with numerical indications 24 showing the amount of overhang between the rim 12 and the edge of the acetabulum of the patient for a given marking 26. These indications 24 may, for example, be provided in the form of a distance (in millimetres) between each horizon marking and the rim 12 or in the form of an angle (for instance the number of degrees) of rotation of the trial cup 10 corresponding to each horizon marking 26.

It is envisaged that the horizon markings 26 can be used to determine an amount of overhang between the rim 12 of the trial cup 10 and the edge of an acetabulum of a patient at a chosen angular position around the rim 12. It is envisaged that markings 16, 18 of the kind described above can be used to determine and record this angular position. To aid this determination, markings 28 and 16 may be provided on the outer surface of the substantially hemispherical shell—these may make it easier to read off the amount of overhang at the correct position around the rim 12.

An example of the use of the trial cup 10 shown in FIGS. 4-6 will now be described with reference also to FIGS. 11A and 11B, which show a pelvis with the trial cup 10 located in an acetabulum 200 thereof.

In a first step, the surgeon may prepare the acetabulum 200 for receiving an acetabular cup implant by progressive reaming until the trial cup 10 fits correctly therein and can be correctly oriented. Once the correct position of the trial cup 10 within the acetabulum has been established, the markings 16, 18 provided around the rim 12 of the trial cup 10 may be used to record the angle of rotation of the trial cup 10 about the cup axis 11 relative to at least one anatomical feature of a patient. For instance, one of the markings 16, 18 may be noted as pointing directly to an anatomical feature such as the ASIS or an osteophyte of the acetabulum. In the example of FIGS. 11A and 11B, the position of the ASIS is indicated by the dotted circles labelled with reference numeral 210. Also in FIG. 11A, the dotted line 212 in FIG. 11A indicates the alignment, in this example, of one of the markings 16 with the ASIS 210. Note that for additional accuracy, the angle of rotation of the trial cup 10 relative to more than one anatomical feature of the patient may be noted.

Having recorded the correct angle of rotation of the trial cup 10, the surgeon may then also determine an amount of overhang between the rim 12 of the trial cup 10 and the edge of the acetabulum in one or more locations around the rim 12. The measurement(s) of overhang may allow the orientation of the trial cup 10 relative to the inclination and ante-version axes to be determined. The location(s) at which the determinations of the amount of overhang are made may themselves be determined using the markings 16, 18. The horizon markings 26 may be used to determine the amount of overhang at these location(s). The combined determination of the angle of rotation of the trial cup 10 about its cup axis 11 the amount of overhang at one or more location around the rim 12 can allow the precise orientation of the trial cup 10 within the acetabulum 200 to be determined.

Having determined and recorded the correct position of the trial cup 10, the surgeon may next remove the trial cup 10 from the acetabulum 200 and replace it with an acetabular cup implant. The surgeon may use the recorded values of the angle of rotation about the cup axis and/or the recorded values of overhang at one or more locations around the rim correctly to orientate the acetabular cup implant, so that it matches the orientation of the trial cup.

To aid the surgeon in correctly matching the orientation of the acetabular cup implant to that of the trial cup 10, as already noted hereinabove the acetabular cup implant may itself include markings 16, 18 around its rim and/or horizon markings 26.

It is envisaged that alternative approaches may be taken for determining the angle of rotation of an acetabular cup (such as a trial cup or a cup implant) about its cup axis. It is also envisaged that alternative approaches may be taken for determining an amount of overhang between a rim of an acetabular cup and an edge of an acetabulum when the acetabular cup is received in the acetabulum. These alternative approaches will be described below.

FIG. 7 shows an example of a protractor 30 for use with an acetabular cup (for instance an acetabular trial cup and/or an acetabular cup implant) in accordance with an embodiment of this invention. The protractor 30 comprises a body portion having an upper surface 32 and a lower surface 34. In this embodiment the body portion is disc shaped for convenient mounting on the acetabular cup, although other shapes may be used. The lower surface 34 is configured to engage with a rim of an acetabular cup such that the centre of the body portion coincides with the cup axis of the acetabular cup. A plurality of markings 40, 42 are located around a periphery of the body portion of the protractor on the upper surface 32. These markings 40, 42 are provided for determining an angle of rotation of the acetabular cup about the cup axis relative to at least one anatomical feature of a patient when the acetabular cup is placed in the acetabulum and the body portion of the protractor 30 is positioned over the rim of the cup.

The markings 40, 42 on the body portion of the protractor 30 may be configured and used in much the same way as described above in relation to the markings 16, 18 in FIGS. 4-6. However, it will be appreciated that when a protractor 30 of the kind shown in FIG. 7 is used, it may not be necessary to provide markings directly on the acetabular cup itself. In particular, it may not be desirable to provide markings directly on an acetabular cup implant.

In some examples, it is envisaged that the surgeon may use a trial cup including its own markings of the kind described above, but then switch to using a protractor of the kind shown in FIG. 7 when aligning the acetabular cup implant. Where a trial cup is not used, the protractor 30 may simply be used to orientate an acetabular cup implant according to a pre-operative plan.

Figure 7A:
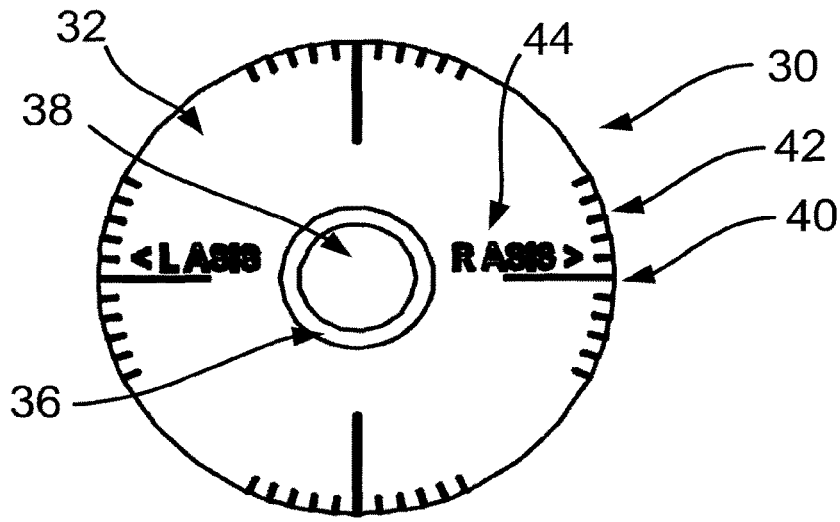
FIGS. 7A-7D show an example of a protractor in accordance with an embodiment of the invention.
Figure 7B:
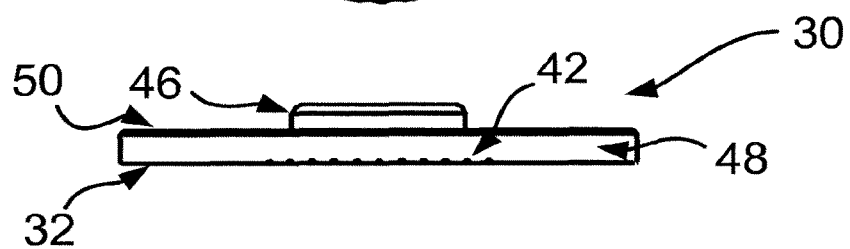
Figure 7C:
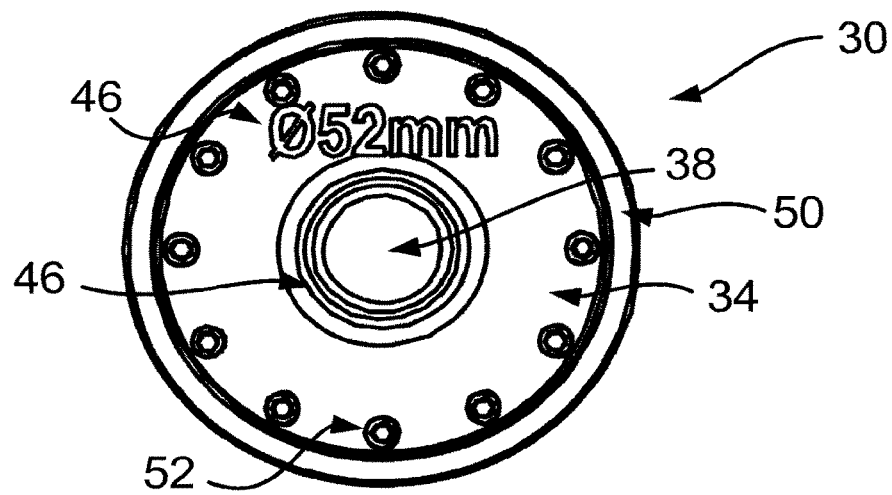

As shown in FIG. 7A, the markings 40, 42 may be supplemented with indications 44 as to important anatomical features of the patient with which those markings may be aligned. In the present example, the indications 44 refer to the left and right ASIS of the patient. In one embodiment, these markings may be aligned with the anatomical features to which they refer and then other markings 40, 42 may be used to determine and record one or more locations for taking measurements of the amount of overhang between the rim of the acetabular cup and the edge of the acetabulum.

Figure 7D:
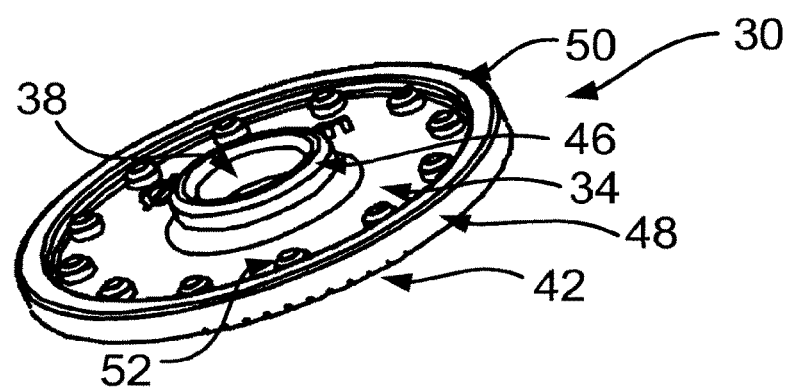

As described above in relation to FIG. 4, the markings 40, 42 of the protractor 30 may include a first type of marking 40 (similar in principle to the markings 18 shown in FIG. 4) and a second type of marking 42 (again similar to the markings 16 shown in FIG. 4). The markings may be provided at regular intervals around the rim. The markings 40, 42 may be provided in one or more groups around the rim (e.g. in FIG. 7A there are four groups of markings). It is envisaged that the markings may extend completely around the rim instead of being provided in groups. As shown in FIG. 7D, in some examples the markings 42 (but also the markings 40) may further extend along an edge 48 of the body portion of the protractor 30 to assist in reading off the angle of the rotation of the acetabular cup when viewing the body portion from one side.

The protractor 30 may be provided in various sizes according to the size of the acetabular cup to be used. The size of each body portion may be indicated thereon (see the indication having reference numeral 46 in FIG. 7C).

The protractor 30 may include a number of engagement portions 52 that are provided on the lower surface 34 of the body portion. These engagement portions 52 can engage with corresponding engagement portions 14 on an acetabular trial cup or cup implant as described above in relation to FIG. 4. The engagement of these engagement portions with each other can allow the protractor 30 to be securely positioned over the rim of the acetabular cup to prevent rotation of the protractor relative to the cup during use, which may otherwise lead to incorrect angular readings being taken. The correct orientation for mounting the protractor 30 on the acetabular cup for "zeroing" the protractor 30 with respect to the cup may be determined in a number of ways. For instance, one of the markings 40, 42 may be aligned with a feature of the acetabular cup such as one of the openings 4 or with a corresponding marking provided on the acetabular cup (e.g. on the rim thereof).

FIG. 8 shows another example of a protractor 70 in accordance with an embodiment of this invention. The protractor 70 in FIG. 8 is similar to that described above in relation to FIG. 7 in a number of ways. For instance, the protractor 70 includes a body portion having an upper surface 83 and a lower surface 84. In this embodiment the body portion is also disc shaped. A number of markings 60, 62 are provided on the upper surface which may be similar in configuration to the markings 40, 42 described above in relation to FIG. 7.

The example of FIG. 8 does not include the engagement portions of the kind described above in relation to FIG. 7, although it is envisaged that these may be included.

Figure 8A:
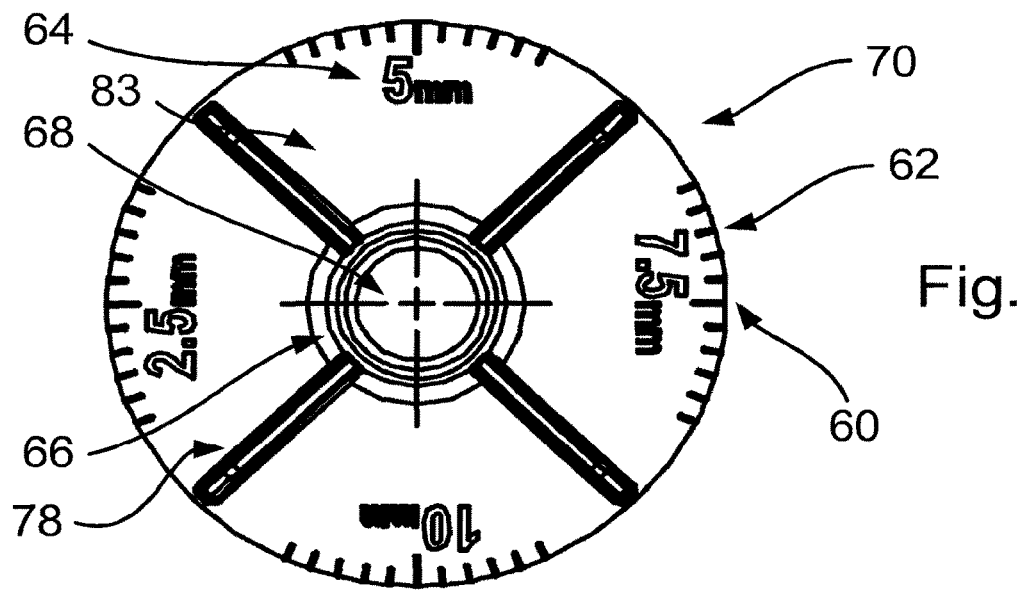
FIGS. 8A-8E show an example of a combined depth gauge and protractor in accordance with an embodiment of the invention.
Figure 8B:
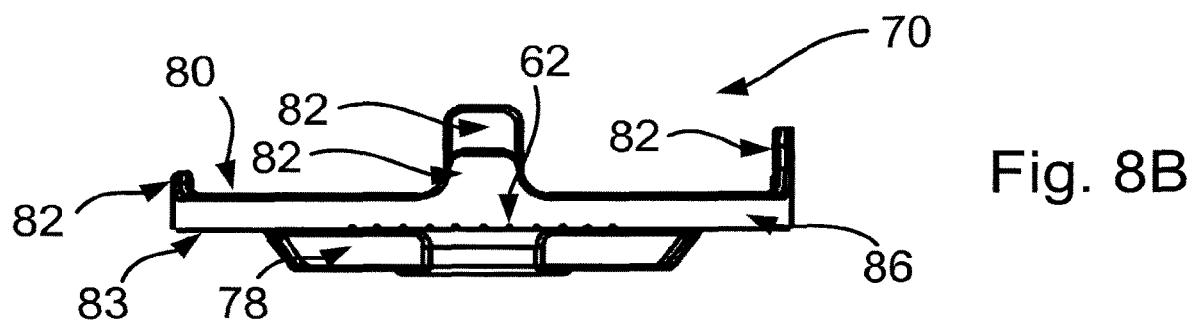
Figure 8C:
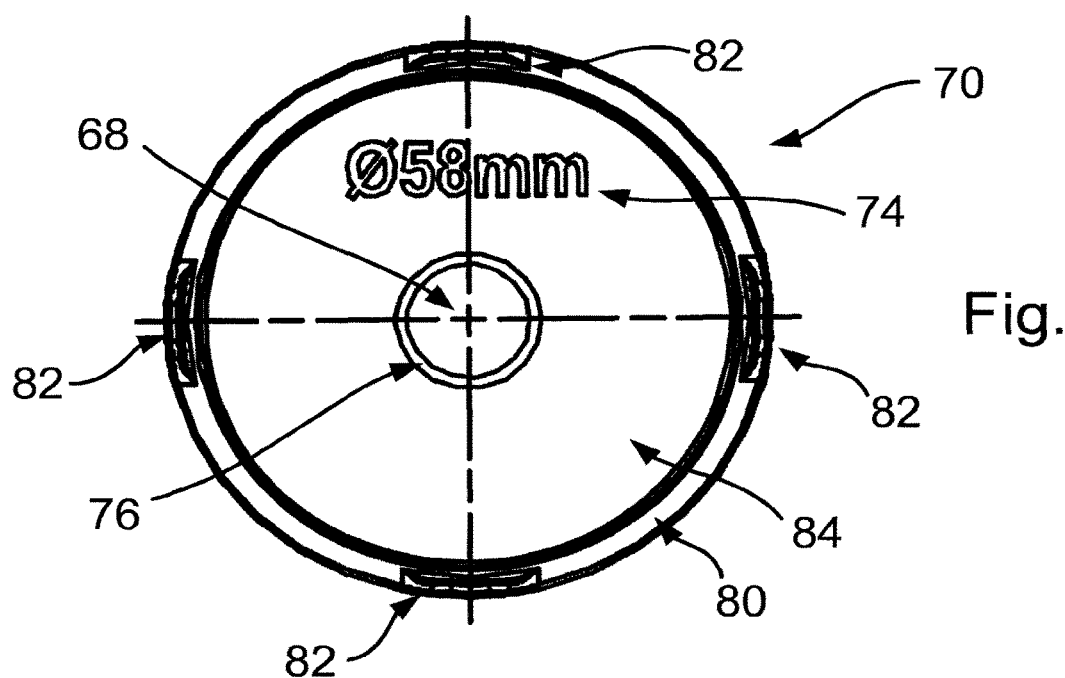
Figure 8D:
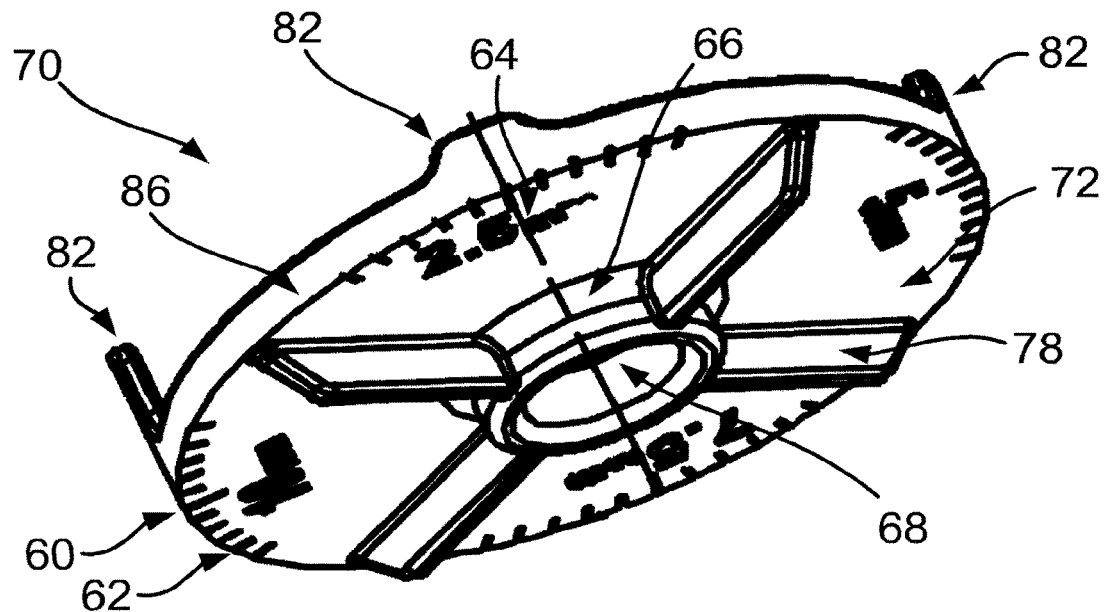

As shown in FIG. 8A and 8B, a number of ridges 78 may be provided on the upper surface 83. These ridges 78 may be used to manipulate the protractor 70 using the surgeon's fingers.

Figure 8E:
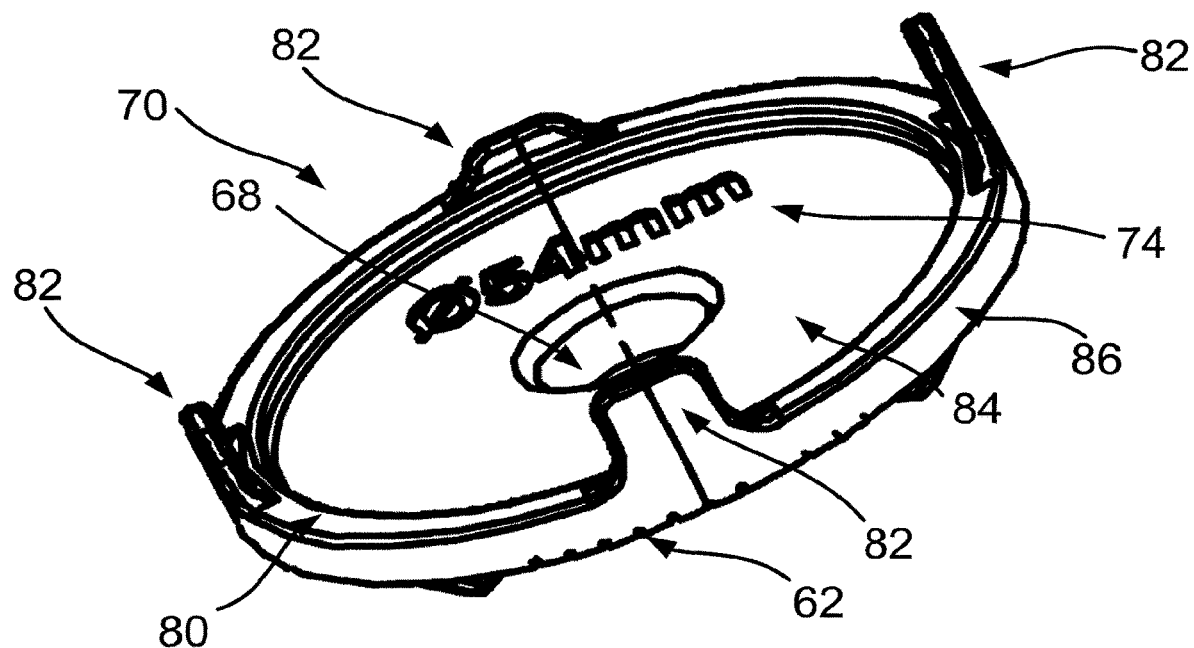

An edge 86 of the body portion of the protractor 70 may also include markings 62 as shown most clearly in FIGS. 8B and 8E. The lower surface 84 may include an indication 74 as to the size of the protractor 70, so that the correct size of protractor 70 may be selected according to the size of the acetabular cup.

In the example of FIG. 8, the protractor 70 is provided with a number of members 82 which extend beneath the body portion of the protractor so as to hang over the rim of an acetabular cup upon which the protractor 70 is received. These members 82 can allow a determination to be made as to an amount of overhang between the rim of the acetabular cup upon which the protractor 70 is mounted and an edge of the acetabulum of the patient. Note that the members 82 shown in FIG. 8 are each of a different length. This may allow the protractor 70 to be used to record overhangs of different sizes by choosing the appropriately sized member 82 and aligning it with the location in which the overhang is to be determined. Once the amount of overhang has been determined, the markings 60, 62 may be used to determine the angular position of the recorded overhang around the cup axis of the acetabular cup with respect to one or more anatomical features of the patient.

Figure 12A:
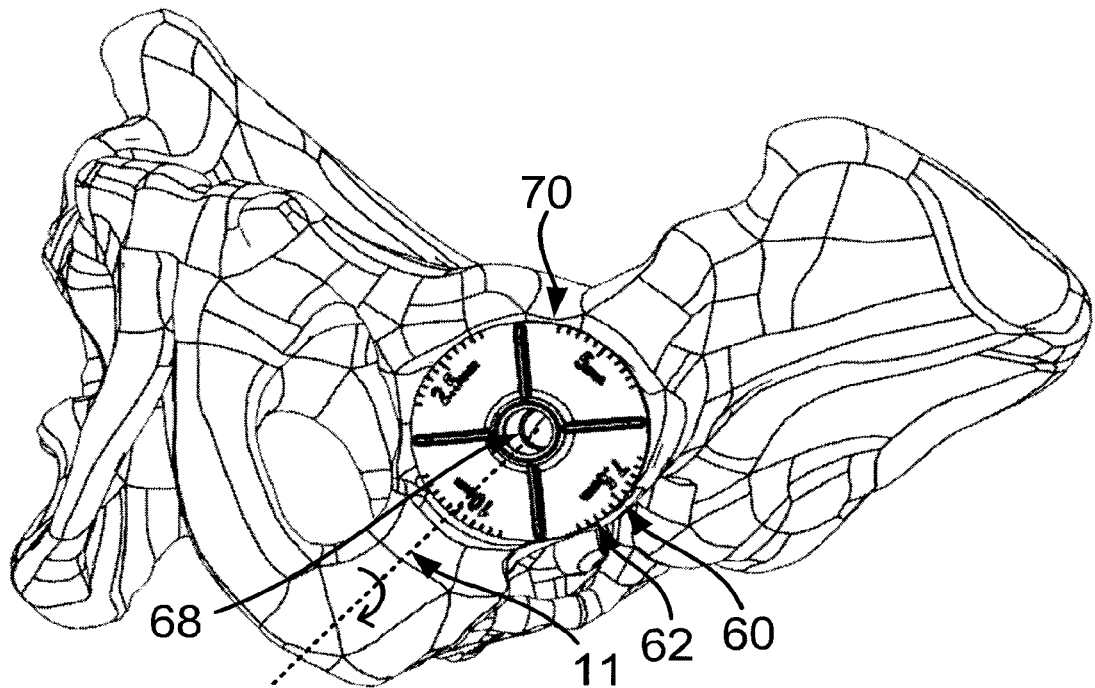
FIGS. 12A and 12B show a pelvis having an acetabular cup implant of the kind shown in FIG. 1 located in an acetabulum thereof, with the combined depth gauge and protractor of FIGS. 8A-8E mounted on the implant, in accordance with an embodiment of the invention.
Figure 12B:
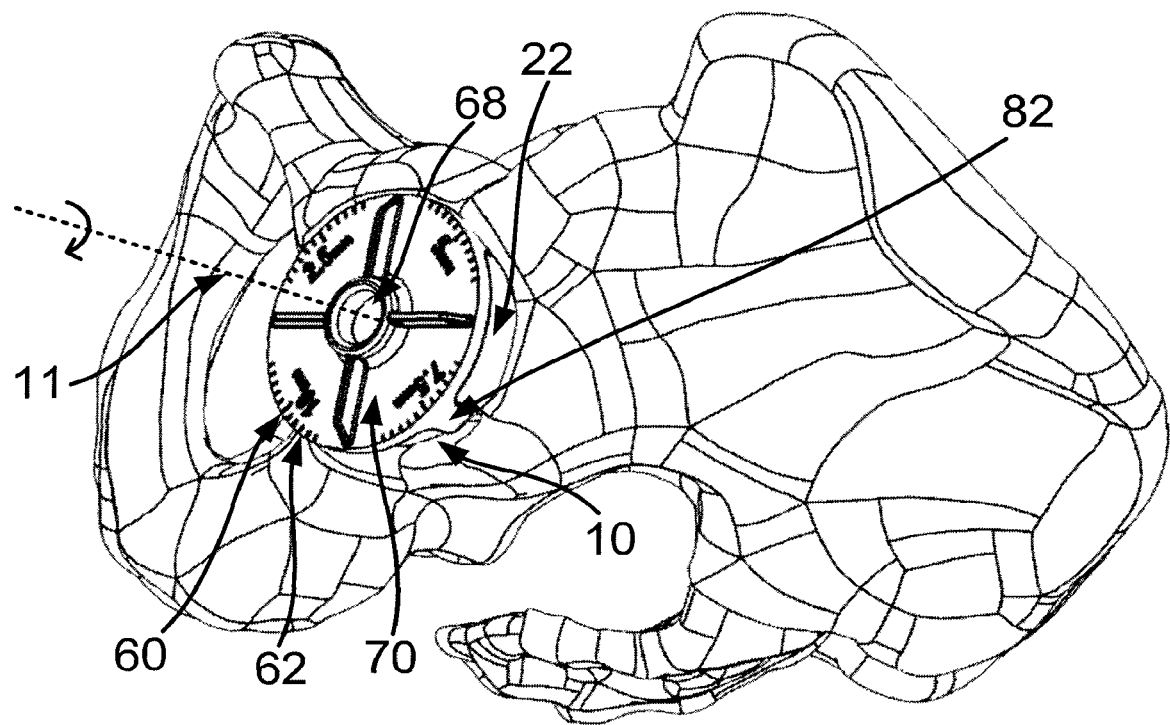

It is envisaged that a protractor 30, 70 of the kind shown in FIG. 7 or 8 can be used in conjunction with an acetabular cup (either a trial cup or a cup implant) which need not necessarily include any markings of its own for determining the rotational position of the cup around its cup axis and/or an amount of overhang between a rim of the cup and the edge of the acetabulum of the patient. It is envisaged that the protractors of FIGS. 7 and 8 may be particularly useful in the case of acetabular cup implants, where it may not be desirable to include markings on the cup implant itself An example of the use of the protractor 70 shown in FIG. 8 will now be described with reference also to FIGS. 12A and 12B. In this example, the acetabular cup is a cup implant 150 of the kind described above in relation to FIGS. 1 and 2, which does not include markings thereon. Nevertheless, it is envisaged that a protractor of the kind described herein may also be used even if the cup implant is of the kind that includes its own rotational and/or horizon markings. Also, as already mentioned above, a protractor of the kind described herein may also be used to determine the orientation of a trial cup.

In FIG. 12, it is assumed that the correct orientation for the cup implant has been determined either using a trial cup or according to a pre-operative plan. It is also assumed that the acetabulum has been correctly prepared to receive the cup implant and that, having placed the cup implant into the acetabulum, the next stage is to orientate it correctly.

As described herein, the correct orientation of the cup implant may be determined using the angle of rotation of the cup implant about its cup axis and/or according to the amount of overhang at one or more locations around the rim of the cup implant. The protractor 70 may be used to ensure correct alignment of the cup implant according to any of these factors.

To orientate the cup implant, the surgeon may place the protractor 70 over the rim of the cup implant. If engagement portions are provided on the protractor, these may be engaged with corresponding engagement portions on the rim of the cup implant. As noted above, the protractor 70 may be placed over the cup implant such that it is "zeroed" with respect to the cup implant. Then, the surgeon may rotate the protractor (and with it the cup implant) until, in accordance with a correct angle determined either using a trial cup or simply as part of a pre-operative plan, one or more of the markings 60, 62 or the protractor 70 are aligned with one or more anatomical features of the patient. At this point, the angle of rotation of the cup implant about its cup axis is correct.

Next, the surgeon may adjust the cup implant until the amount of overhang between a rim of the cup implant and an edge of the acetabulum matches a correct orientation for the cup implant. Again, the correct amount of overhang may have been determined using a trial cup or as part of a pre-operative plan. The correct position(s) around the rim of the implant for determining the amount of overhang may be noted using the markings 60, 62. These position(s) may be marked with ink at the edge of the acetabulum. The protractor 70 may then be lifted off the cup implant and replaced so that one of the members 82, which has a length equal to the required amount of overhang, is placed in the correct location around the rim. The surgeon may then adjust the orientation of the cup implant so that a distal end of the member 82 abuts the edge of the acetabulum. This process may be repeated at further location(s) around the rim if required.

Figure 9:
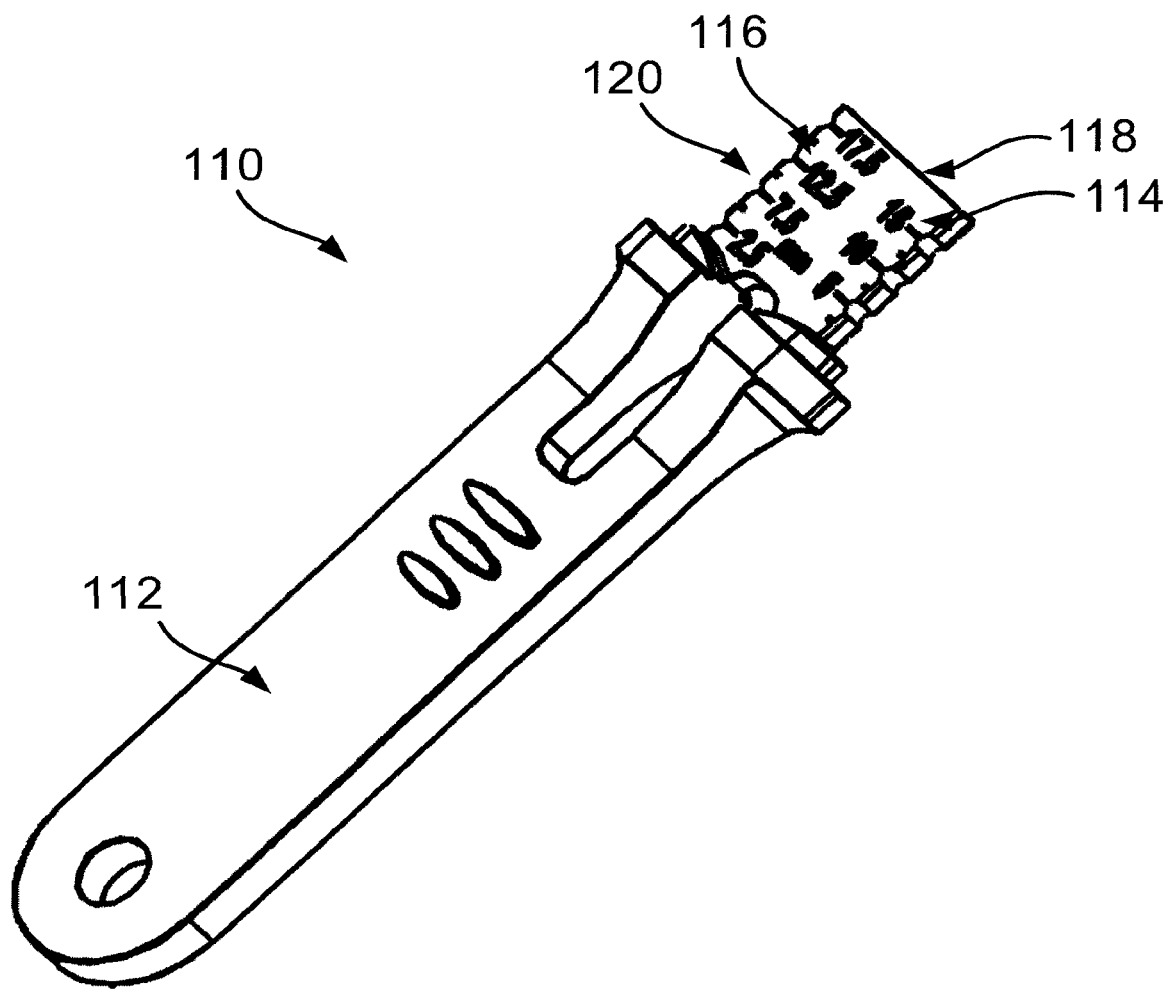
FIG. 9 shows an example of a rim caliper in accordance with an embodiment of the invention.
Figure 10E:
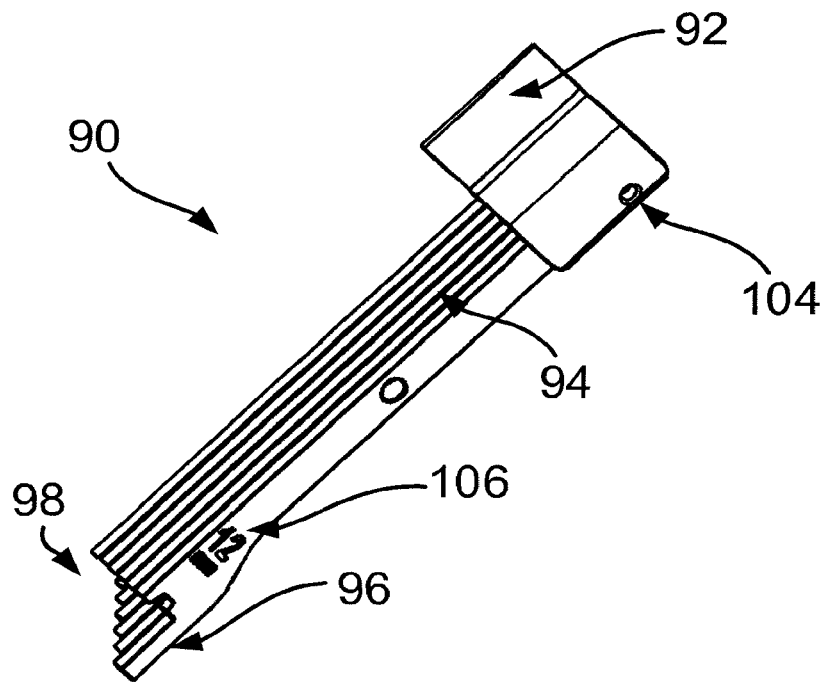
Figure 10F:
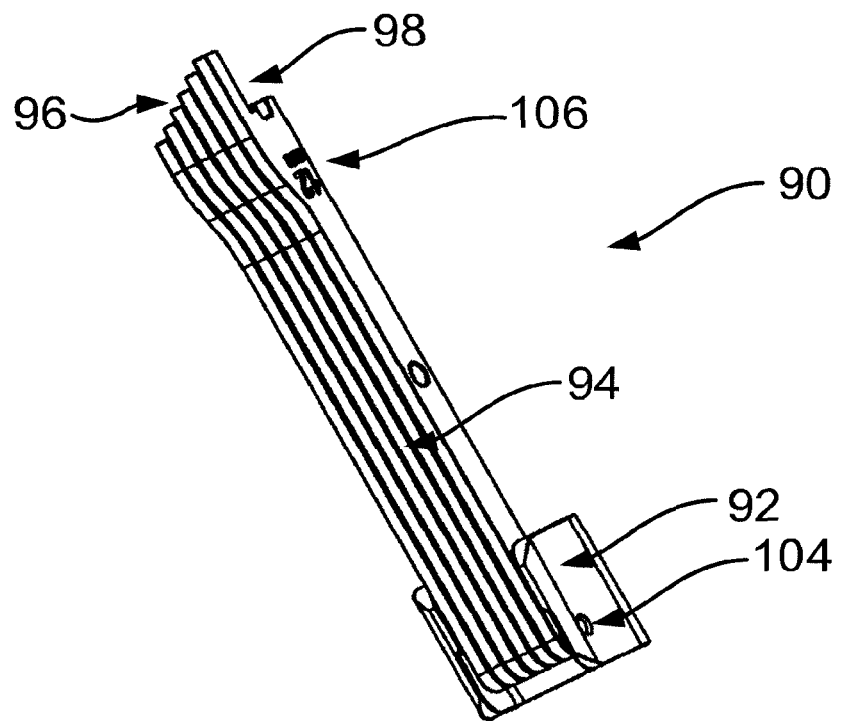

Another way to measure the amount of overhang at one or more locations around the rim of an acetabular cup is to use a rim caliper. An example of a rim caliper 110 is shown in FIG. 9. The rim caliper 110 includes a handle 112 and a caliper portion 120 which is located at a distal end of the handle 112. The caliper portion 120 has a distal end 118 which, during use may be placed against an edge of the acetabulum of the patient in order to read off the amount of overhang between the rim of an acetabular cup such as an acetabular trial cup or an acetabular cup implant. To assist in reading off the amount of overhang, the caliper portion may be provided with a gauge having numerical indications 114, 116 of the overhang.

The rim caliper 110 may be used instead of the horizon markings discussed above and/or instead of the members which extend beneath the body portion of a protractor to determine the amount of overhang at one or more locations around the rim of an acetabular cup. In some examples, markings on an acetabular cup or on a protractor of the kind described above may be used to determine the angular position(s) of the location(s) around the rim (i.e. about the cup axis) of the cup at which the rim calliper 110 is used to measure the overhang.

FIGS. 10A-10F show various views of a depth gauge tool 90 that may be used to orientate an acetabular cup implant during surgery.

The depth gauge tool 90 includes a base 92. The base 92 includes an aperture 102 for receiving an impactor for pushing an acetabular cup implant into an acetabulum of a patient. The impactor tool includes a rod that passes through the aperture 102 and which may be attached (e.g. using corresponding screw threads) to an opening located at a pole of the substantially hemispherical shell of the acetabular cup implant (e.g. see the opening 156 shown in FIG. 1). Once attached to the acetabular cup implant, the rod extends along the cup axis thereof. To insert the acetabular cup implant into the acetabulum of a patient, the surgeon may use a hammer to strike a proximal end of the rod.

If a protractor of the kind described above is used, the rod may also pass thorough an opening located in the body portion thereof. Note that the openings 38, 68 in the protractors shown in FIGS. 7 and 8 are located at a centre of the body portion to allow the rod to extend along the cup axis while the edges of the body portion engage with the rim of the cup.

The depth gauge tool 90 includes features that may allow the acetabular cup implant to be aligned prior to insertion of the cup into the acetabulum. In particular, the depth gauge tool 90 includes a plurality of elongate arms 94 which are pivotably attached to the base 92 at pivot point 104. Each arm 94 has a distal end that includes an abutment surface 98 for abutting a rim of the acetabular cup implant. In use, any of the arms may be rotated about pivot point 104 so that it extends substantially parallel to the rod passing through the aperture 102, thereby to engage with the rim of the acetabular cup implant. Each arm 94 also includes a finger 96 that is configured to extend over the rim of the acetabular cup implant to abut an edge of the acetabulum. The finger 96 of each arm 94 may have a different length. Accordingly, the surgeon may select the arm having the desired finger length. The arms 92 may be provided with indications 106 as the finger length for that arm 94 to aid the surgeon in selecting the correct arm 94. The remaining arms 94 may be rotated to one side about the pivot point 104, so that they do not interfere with the operation of the selected arm 94.

The arms 94 of the depth gauge tool 90 may be used to determine an amount of overhang between the rim of the acetabular cup implant and the edge of the acetabulum of the patient. For instance, a correct amount of overhang may have been determined for one or more locations around the rim of the cup as part of a pre-operative plan or using a trial cup. The surgeon may use one of more of the arms 94 to adjust the amount of overhang between the rim of the acetabular cup implant and the edge of the acetabulum according to the correct amount at one or more locations around the rim of the acetabular cup implant. To determine the correct location(s) around the rim of the acetabular cup implant for using the arms 94 to determine the amount of overhang, markings such as those described above (e.g. such as the markings 16, 18 or the markings 40, 42, 60, 62) either on the implant itself or on a protractor may be used. These markings may initially be used to correctly orientate the acetabular cup implant in terms of its angle of rotation about the cup axis relative to at least one anatomical feature prior to use of the depth gauge tool 90.

Having correctly aligned the acetabular cup implant, the surgeon may strike a proximal end of the rod passing through the aperture 102.

It will be appreciated that various approaches have been described herein for:

- determining an angle of rotation of an acetabular cup about a cup axis relative to at least one anatomical feature of a patient (e.g. using markings provided on the cup itself or markings on a protractor that may be mounted on the cup);
- determining an amount of overhang between a rim of an acetabular cup and an edge of the acetabulum of the patient (e.g. using horizon markings located on the acetabular cup itself; using a number of members which extend beneath the body portion of a protractor as described in relation to FIG. 8, using a rim calliper as described in relation to FIG. 9, or using a depth gauge tool as described in relation to FIG. 10).

It will also be appreciated that various combinations of these approaches may be used during any particular surgical procedure.

Figure 13A:
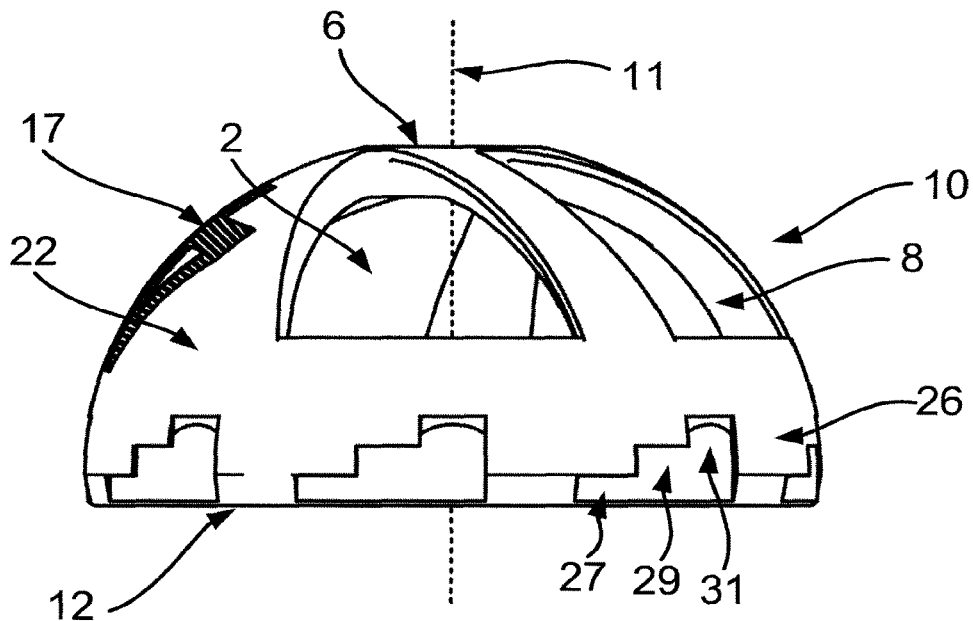
FIGS. 13A-13C show an example of a trial cup in accordance with another embodiment of the invention.
Figure 13B:
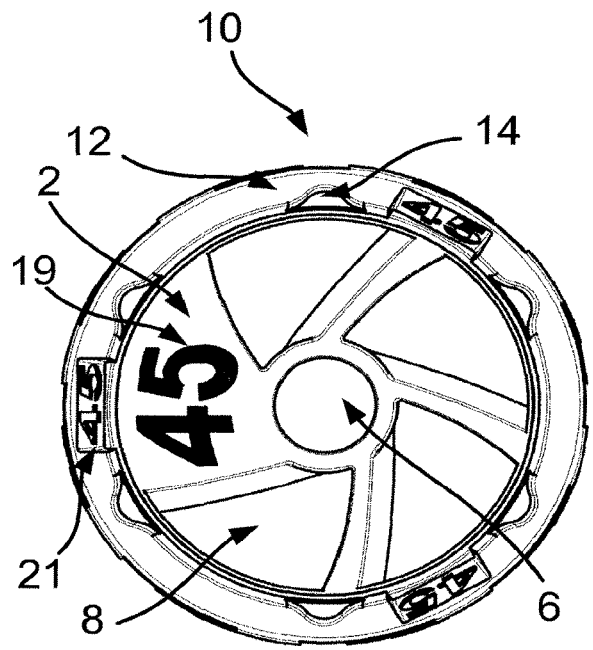
Figure 13C:
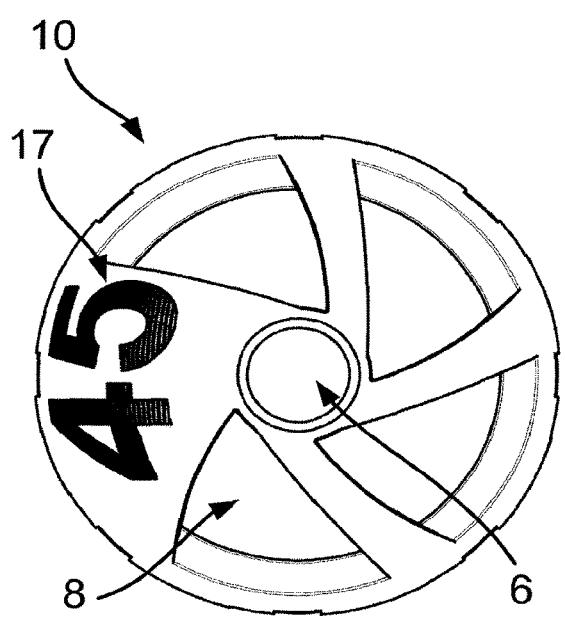
Figure 14C:
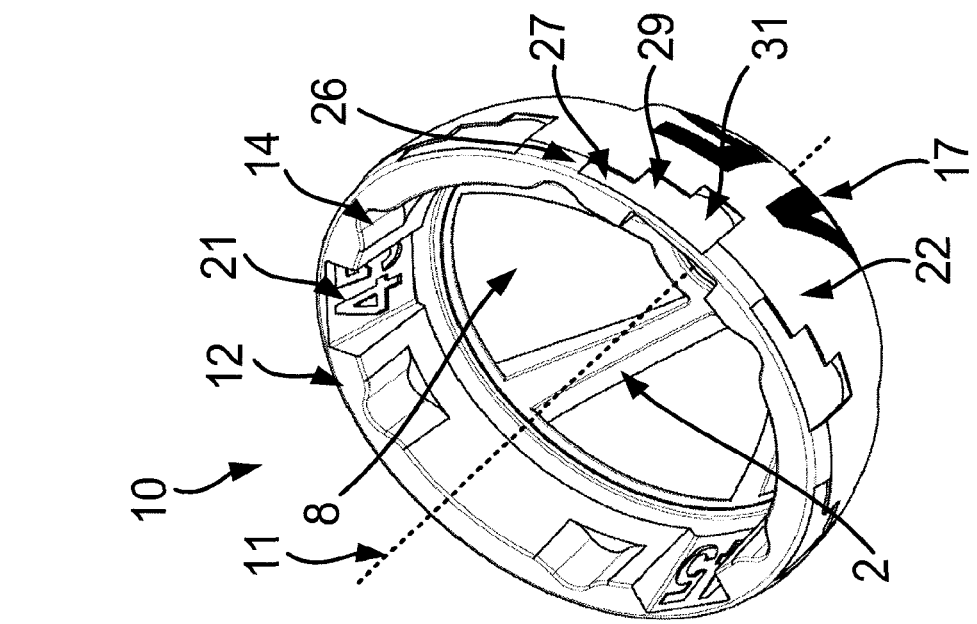
FIGS. 14A-14C show further views of the trial cup of FIGS. 13A-13C.
Figure 14B:
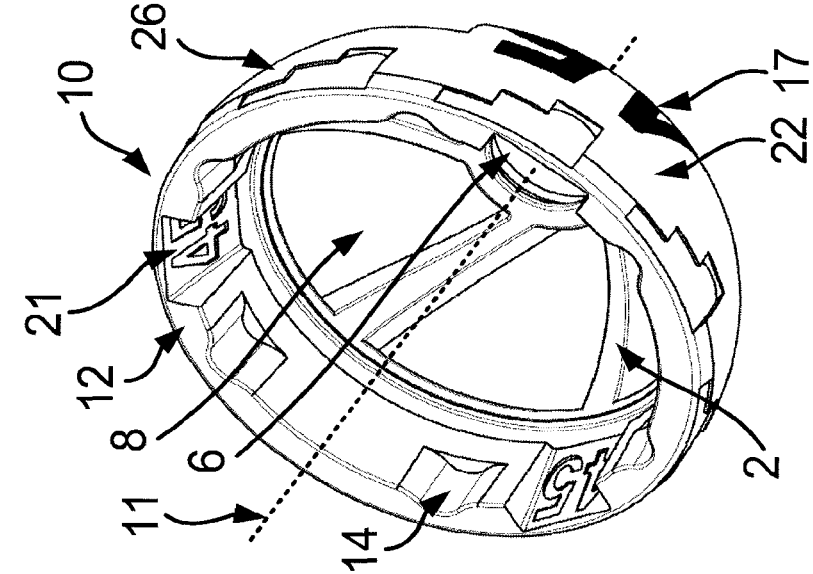
Figure 14A:
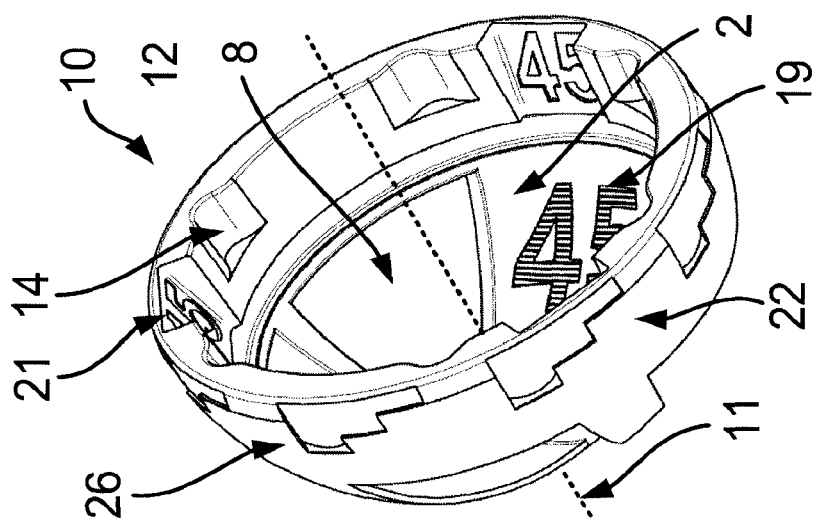

FIGS. 13A-13C show an example of an acetabular trial cup 10 in accordance with another embodiment of the invention. Further views of the acetabular trial cup 10 are shown in FIGS. 14A-14C.

The acetabular trial cup 10 in this example has a number of features in common with the acetabular trial cup 10 described above in relation to FIGS. 4 to 6. Examples of these are summarised below.

The acetabular trial cup 10 has a substantially hemispherical shell that has an inner surface 2 and an outer surface 22. The acetabular trial cup 10 may include an opening 6 located at a pole of the hemispherical shell, and may further include a number of openings 8 positioned around the substantially hemispherical shell, similar to the opening 6 and openings 8 of the cup of FIG. 4-6.

The acetabular trial cup 10 has a rim 12. A number of engagement portions 14 may be positioned around the rim 12, similar to the engagement portions on the rim 12 of the cup 10 of FIGS. 4-6.

The acetabular trial cup 10 has a cup axis 11, which passes through the pole of the substantially hemispherical shell of the acetabular trial cup 10 and which is substantially perpendicular to a plane containing the rim 12. The cup axis 11 is shown schematically by the dotted line labelled 11 in FIGS. 13A and 14A-14C.

In this embodiment, the acetabular trial cup 10 may include a number of indicia which may clearly identify the size of the acetabular trial cup 10. The indicia may include a numeral indicia, for instance identifying the diameter of the acetabular trial cup 10 at the rim 12. The indicia may include one or more indicia 17 located on the outer surface 22 of the hemispherical shell. The indicia may also include one or more indicia 19 located on the inner surface 2 of the hemispherical shell. The indicia may further include one or more indicia 21 located on the inner surface 2 of the hemispherical shell, adjacent the rim 12. The indicia may assist in preventing inadvertent selection of the incorrect size of cup, for instance from a kit including several different cup sizes. Indicia of this kind may also be provided on an acetabular cup implant of the kind described herein.

The acetabular trial cup 10 in this embodiment includes a plurality of horizon markings 26. The horizon markings 26 are located on the outer surface 22 of the substantially hemispherical shell of the acetabular trial cup 10. As described previous in relation to the cup 10 of FIG. 4-6, the horizon markings 26 may be used for determining an amount of overhang between the rim 12 of the acetabular trial cup 10 and an edge of the acetabulum of the patient when the acetabular trial cup 10 is received within the acetabulum of the patient.

Although the horizon markings 26 are described here in the context of an acetabular trial cup 10, it is envisaged that horizon markings of this kind may be provided on an acetabular cup implant (for instance of the kind described above in relation to FIG. 1), to allow an amount of overhang between the rim of the acetabular cup implant and an edge of the acetabulum of the patient to be determined when the acetabular cup implant is received within the acetabulum of the patient.

The horizon markings 26 in this embodiment are stepped markings, each comprising a plurality of steps 27, 29, 31. Each step 27, 29, 31 may be substantially oblong. Each step 27, 29, 31 may extend from the rim 12 of the acetabular trial cup 10, on the outer surface 22 of the hemispherical shell, towards the pole of the hemispherical shell. The distance that each step 27, 29, 31 extends from the rim 12 towards the pole of the hemispherical shell may correspond to an amount of overhang between the rim 12 and the edge of the acetabulum of the patient. In particular, the location of a bottom edge of each step 27, 29, 31 (namely an edge of each step distal the rim 12) may correspond to an amount of overhang. The increments between the steps may fixed, e.g. at 1, 2, 2.5, or 5 degrees. In use, the surgeon may inspect the locations of the bottom edges of the steps 27, 29, 31 relative to the edge of the acetabulum to determine the amount of overhang. As with the horizon markings of the acetabular trial cup 10 described above in relation to FIG. 4-6, it is envisaged that the steps 27, 29, 31 may be provided with numerical indications of the amount of overhang associated with each step 27, 29, 31.

The steps 27, 29, 31 of each horizon marking 26 are grouped together, for instance in the example shown in the Figures, they are located adjacent each other so that each step touches its neighbouring step (however, it is envisaged that each step 27, 29, 31 may be separated slightly).

Although each horizon marking 26 in the present example includes three steps, it is envisaged that each horizon marking 26 may include two, three, four, five or more steps. A greater number of steps can allow the increments between each step to be reduced, potentially allowing more accurate measurements of the overhang between the rim 12 and the edge of the acetabulum to be made. On the other hand, if a large number of steps are provided, the clarity of the horizon markings may be reduced. In this respect, it is envisaged that the provision of three steps 27, 29, 31 as shown in the present example may be optimal.

As can be seen in FIGS. 13A and 14A-14C, the acetabular trial cup 10 may be provided with a plurality of horizon markings 26, each horizon marking including a plurality of steps 27, 29, 31. Each horizon marking 26 may be located at a different position around the rim of the acetabular trial cup 10. The horizon markings 26 may be equally spaced around the rim, as is shown in the Figures.

Although not shown in the present example, it is envisaged that an acetabular trial cup 10 of the kind shown in the FIGS. 13 and 14 may also include a plurality of markings 16, 18 of the kind described in relation to the cup 10 of FIGS. 4-6. As described previously, these marking 16, 18 may be located around the rim 12 for determining an angle of rotation of the acetabular trial cup 10 about the cup axis 11, relative to at least one anatomical feature of a patient when the acetabular trial cup 10 is placed in an acetabulum of the patient. As described herein, the markings 16, 18 and the horizon markings 26 may be used together to determine the orientation of the acetabular trial cup 10 in the acetabulum. The angles determined using the markings 16, 18 and the horizon markings 26 may be used subsequently to orient an acetabular cup implant 10, which may include similar markings, in the acetabulum.

In some examples it is envisaged that the horizon markings 26 may themselves also constitute a plurality of markings located around the rim 12 for determining an angle of rotation of the acetabular trial cup 10 about the cup axis 11 relative to at least one anatomical feature of a patient when the acetabular trial cup 10 is placed in an acetabulum of the patient. In particular, it is envisaged that the positions of the horizon markings 26 around the rim 12 may correspond to predetermined angles around the cup axis 11. Moreover, the steps 27, 29, 31 of each horizon marking 26 may also each correspond to such a predetermined angle. In this way, the surgeon may be able to read off the angle of rotation of the acetabular trial cup 10 about the cup axis 11 relative to at least one anatomical feature of a patient by inspecting the angular location of a given horizon marking 26 and/or step 27, 29, 31 relative to the anatomical feature. In the present example, the acetabular trial cup 10 includes eight equally spaced horizon markings 26. The angular increment between the location of each horizon marking 26 around the cup axis is accordingly 45 degrees. This angular increment would depend upon the number of horizon markings that are provided. Moreover, the steps 27, 29, 31 within each horizon marking 26 may be equally spaced at an incremental angle of, for instance, 1, 2, 4, or 5 degrees, allowing for a more granular, local determination of the angle of rotation of the acetabular trial cup 10 about the cup axis 11 relative to at least one anatomical feature of a patient, by inspecting the angular location of a given step 27, 29, 31 relative to the anatomical feature.

Figure 15A:
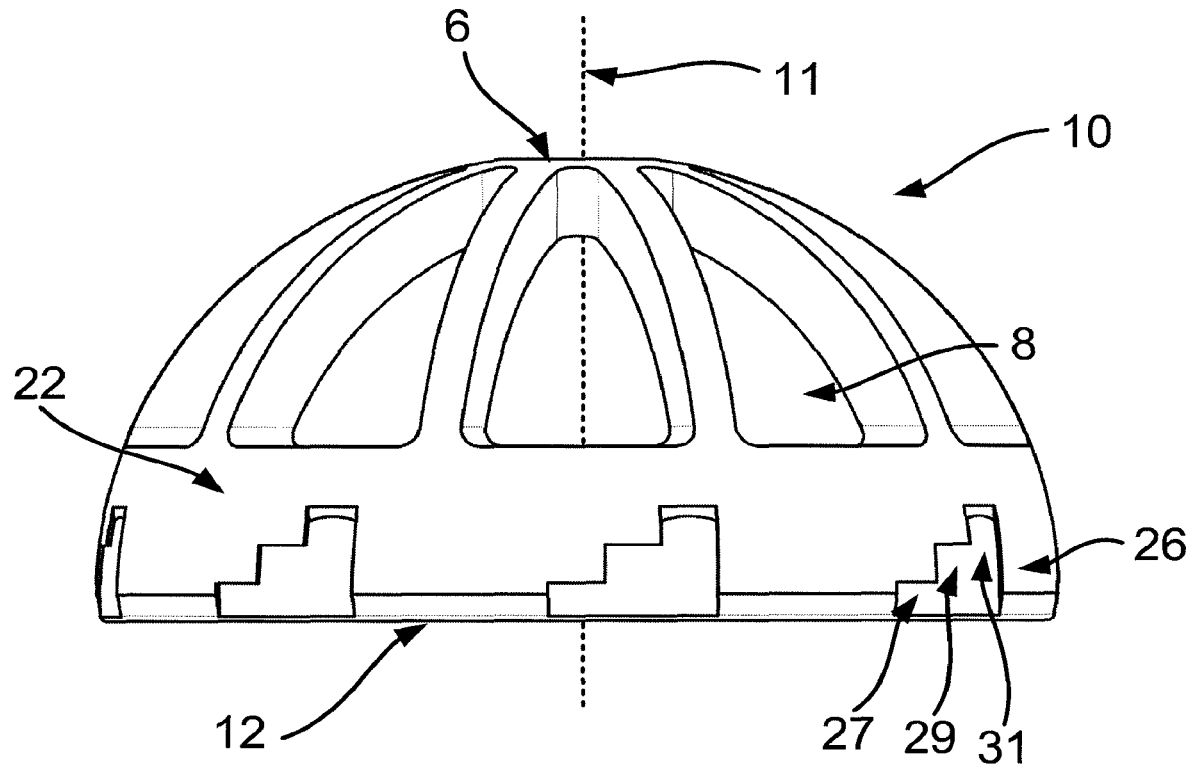
FIGS. 15A and 15B show a comparison of two different sizes of trial cup including horizon markings of the kind shown in FIGS. 13A-13C and 14A-14C.
Figure 15B:
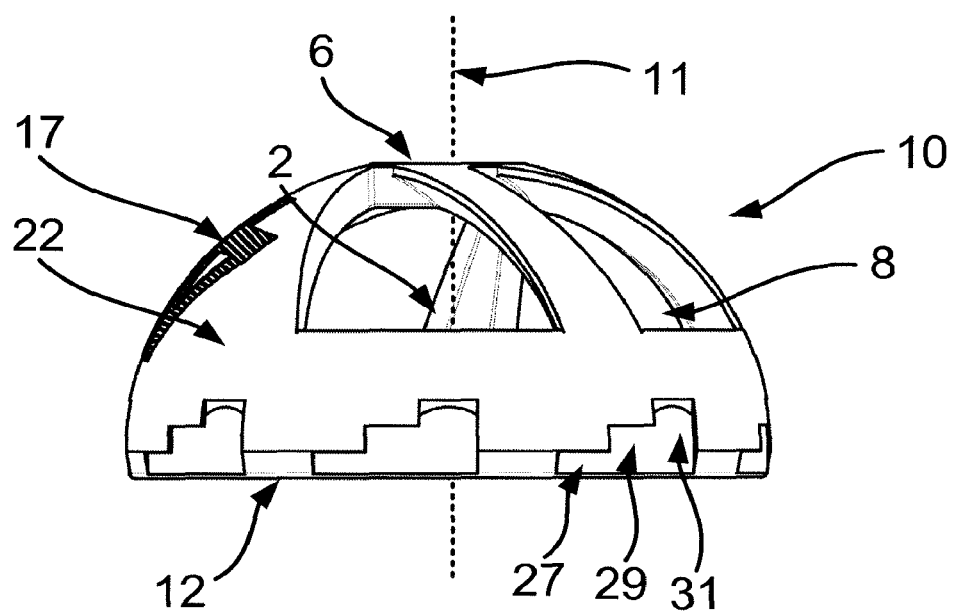

FIGS. 15A and 15B show a comparison of two different sizes of trial cup including horizon markings 26 of the kind shown in FIGS. 13A-13C and 14A-14C. As can be seen from comparison of FIGS. 15A and 15B, the size of the horizon markings 26 in this example scales with the size of the cup. This allows each of the steps 27, 29, 31 of each horizon marking 26 to indicate the same horizon angles. This can make surgical kits including differently sized acetabular cups 10 incorporating the horizon markings 26 easier to use, since the steps 27, 29, 31 may each indicate the a common set of angles (e.g. the step 27 may indicate a horizon angle of 2 degrees, irrespective of the size of the cup 10, and so on).

Figure 11A:
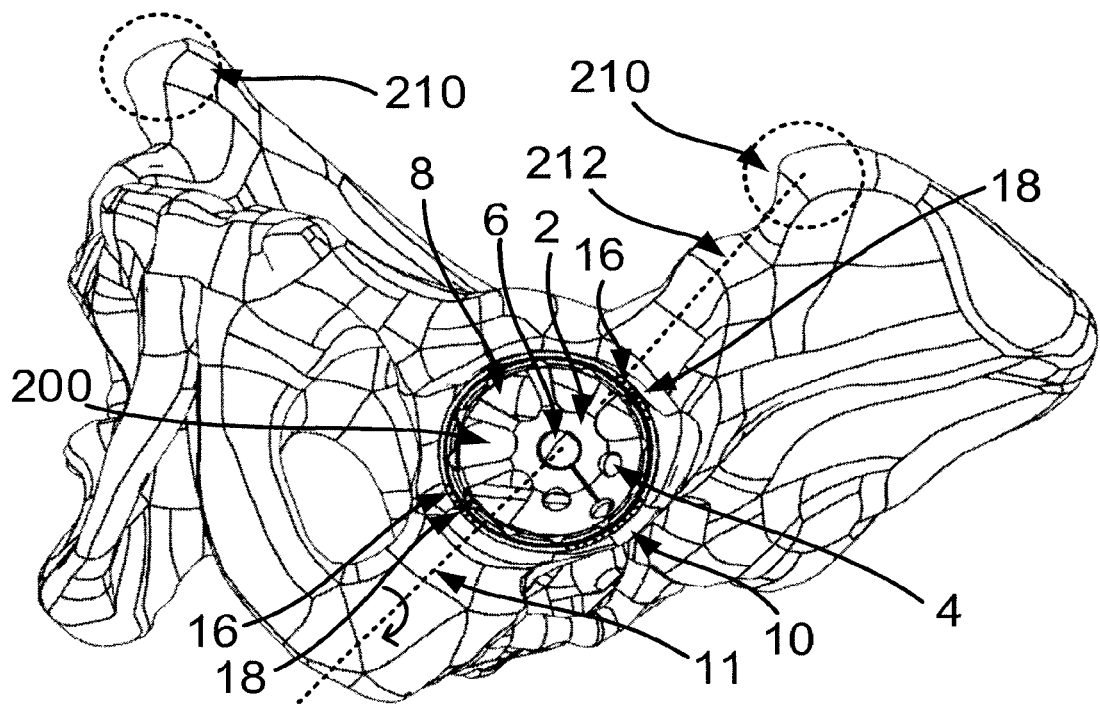
FIGS. 11A and 11B show a pelvis having the trial cup of FIGS. 4-6 located in an acetabulum thereof, in accordance with an embodiment of the invention.
Figure 11B:
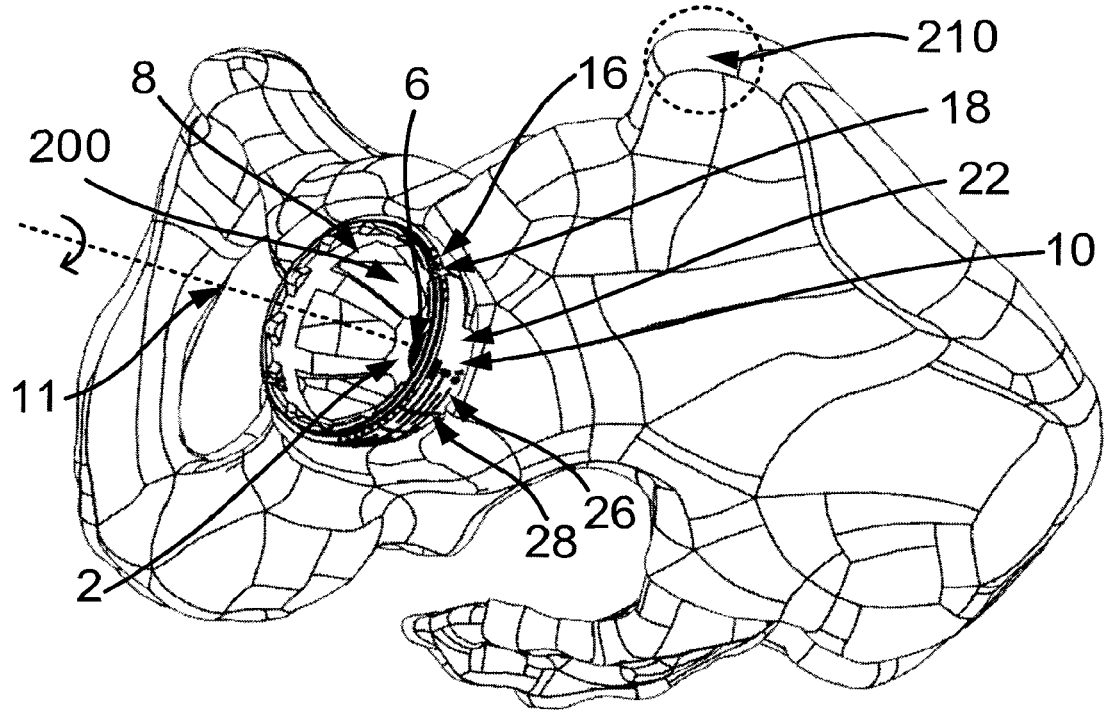

It is envisaged that an acetabular trial cup 10 of the kind shown in the FIGS. 13 to 15 may be used in much the same way as the cup 10 described above in relation to FIGS. 4 to 6 (in this respect, refer also to FIGS. 11A and 11B).

In accordance with an embodiment of the invention, an acetabular cup such as a trial cup or cup implant of the kind described herein may be manufactured using metal injection molding (MIM). The MIM process involves mixing a metal powder with a binding agent to create a fluid slurry which can be melted and injected into an injection molding tool. The slurry sets in the tool and the molded parts are removed in a "green" state. In this state, the molded parts are fragile and slightly larger than the final product. The parts are then transferred to a kiln and heated so that the binding agent melts out or vaporizes while the metal powder fuses to a nearly 100% dense matrix. In some examples, at least some of the binding agent may be removed (e.g. using solvents) prior to placing the parts in the kiln.

The resulting parts may be substantially indistinguishable from a machined part, but the use of MIM can conveniently allow components having complex geometries and/or fine surface details to be produced in high volumes.

MIM lends itself to the manufacture of an acetabular cup such as an acetabular trial cup of acetabular cup implant of the kind described herein, since it can conveniently allow details such as the rim markings and/or horizon markings to be created on the surface of the hemispherical shell. In particular, MIM may allow the markings to be produced directly from the molding process in a precise and repeatable fashion relative to the rest of the cup, whereby the accuracy of the angles determined using the markings may be improved. It is also envisaged that the MIM process may allow the outer surface of the hemispherical shell of the acetabular cup to be provided with features such as grooves, which may improve the grip between the acetabular cup and the surface of the acetabulum. It is further envisaged that the rim markings and/or horizon markings described herein may themselves act to improve the grip between the acetabular cup and the acetabulum.

A restriction of the MIM process is that it may require the design of the acetabular cup to be "open and shut", that is to say made with a positive mould draft in both directions from the split line. The design of the acetabular trial cups shown in FIGS. 13 to 15 fulfill this requirement.

In some embodiments, there may be provided a surgical kit including a combination of tools of the kind described above for use during hip replacement.

Accordingly, there has been described an apparatus and method for aligning an acetabular cup. The apparatus may include an acetabular cup and/or a protractor and/or a depth gauge tool and may be provided in the form of a surgical kit. Components of the apparatus may allow an angle of rotation of an acetabular cup about an axis of the cup relative to an anatomical feature of a patient to be determined when the acetabular cup implant is placed in the acetabulum of the patient. Components of the apparatus may allow an amount of overhang between a rim of an acetabular cup and an edge of the acetabulum to be determined. The acetabular cup may be an acetabular trial cup or and acetabular cup implant. Embodiments of the invention may allow both the angle of rotation about the cup axis and the amount of overhang between the rim and the acetabulum edge to be determined.

Although particular embodiments of the invention have been described, it will be appreciated that many modifications/additions and/or substitutions may be made within the scope of the claimed invention.

The invention claimed is:
1. An orthopaedic surgical system, comprising:
an acetabular component having (i) a substantially hemispherically-shaped shell that defines a substantially circularly-shaped rim; (ii) an opening formed in a pole of the hemispherically-shaped shell, wherein a cup axis passes through the opening and is substantially perpendicular to a plane defined by the rim; and (iii) a plurality of engagement portions formed radially around the rim, and
a protractor having (i) a body portion having an upper surface and a lower surface, wherein the lower surface is configured to engage with the rim of the acetabular component such that a center of the body portion is aligned with the cup axis of the acetabular component; (ii) a plurality of engagement portions located on the lower surface of the body portion and configured to be received into the corresponding plurality of engagement portions of the acetabular component to prevent rotation of the protractor relative to the acetabular component about the cup axis when the body portion of the protractor is positioned in engagement with the rim of the acetabular component; and (iii) a plurality of markings located around a periphery of the body portion on the upper surface, for determining an angle of rotation of the acetabular component about the cup axis relative to at least one anatomical feature of a patient when the acetabular component is placed in an acetabulum of the patient and the body portion is positioned in engagement with the rim of the acetabular component.

2. The orthopaedic surgical system of claim 1 wherein the protractor includes at least one member extending beneath the body portion to hang over the rim of the acetabular component for determining an amount of overhang between the rim of the acetabular component and an edge of the acetabulum of the patient.

3. The orthopaedic surgical system of claim 1, wherein the plurality of markings of the protractor comprise a plurality of substantially equally spaced tick marks located around a periphery of the body portion on the upper surface.

4. The orthopaedic surgical system of claim 1, wherein the plurality of markings of the protractor located around a periphery of the body portion on the upper surface are provided in at least two separate groups.

5. The orthopaedic surgical system of claim 1, wherein the acetabular component comprises an acetabular cup implant.

6. The orthopaedic surgical system of claim 1, wherein the acetabular component comprises an acetabular trial cup.

\* \* \* \* \*